US009050299B2

(12) United States Patent
Bankiewicz

(10) Patent No.: US 9,050,299 B2
(45) Date of Patent: Jun. 9, 2015

(54) ADMINISTRATION OF GROWTH FACTORS FOR THE TREATMENT OF CNS DISORDERS

(71) Applicant: The Regents of the University of California, Oakland, CA (US)

(72) Inventor: Krystof S. Bankiewicz, Oakland, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 13/781,174

(22) Filed: Feb. 28, 2013

(65) Prior Publication Data

US 2014/0017297 A1    Jan. 16, 2014

Related U.S. Application Data

(60) Division of application No. 13/078,357, filed on Apr. 1, 2011, now Pat. No. 8,409,548, which is a continuation of application No. 11/740,124, filed on Apr. 25, 2007, now Pat. No. 7,922,999.

(60) Provisional application No. 60/795,012, filed on Apr. 25, 2006.

(51) Int. Cl.
| | |
|---|---|
| A61K 38/00 | (2006.01) |
| A61K 38/18 | (2006.01) |
| A61P 3/04 | (2006.01) |
| A61P 25/00 | (2006.01) |
| A61K 9/00 | (2006.01) |
| A61K 49/04 | (2006.01) |
| A61K 49/18 | (2006.01) |
| A61K 48/00 | (2006.01) |
| A61K 33/24 | (2006.01) |

(52) U.S. Cl.
CPC .............. *A61K 38/185* (2013.01); *A61K 9/0085* (2013.01); *A61K 49/0466* (2013.01); *A61K 49/1812* (2013.01); *A61K 48/0083* (2013.01); *A61K 33/24* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,676,928 A | 10/1997 | Klaveness et al. | |
| 5,720,720 A | 2/1998 | Laske et al. | |
| 5,731,284 A | 3/1998 | Williams | |
| 5,733,875 A | 3/1998 | Martin | |
| 5,741,778 A | 4/1998 | Martin et al. | |
| 5,830,857 A | 11/1998 | Carnahan et al. | |
| 5,843,473 A | 12/1998 | Woodle et al. | |
| 5,846,565 A | 12/1998 | Brem et al. | |
| 6,042,579 A | 3/2000 | Elsberry | |
| 6,180,613 B1 | 1/2001 | Kaplitt et al. | |
| 6,245,330 B1 | 6/2001 | Horellou et al. | |
| RE37,410 E | 10/2001 | Brem | |
| 6,632,427 B1 | 10/2003 | Finiels et al. | |
| 6,790,824 B1 | 9/2004 | Unsicker et al. | |
| 6,800,281 B2 | 10/2004 | Aebischer et al. | |
| 6,815,431 B2 | 11/2004 | Tuszynski | |
| 7,018,628 B1 | 3/2006 | Sarkis et al. | |
| 7,157,435 B2 | 1/2007 | Tuszynski et al. | |
| 7,182,944 B2 | 2/2007 | Bankiewicz | |
| 7,244,423 B2 | 7/2007 | Tuszynski | |
| 7,371,225 B2 | 5/2008 | Oldfield et al. | |
| 2002/0114780 A1 | 8/2002 | Bankiewicz et al. | |
| 2002/0141980 A1 | 10/2002 | Bankiewicz et al. | |
| 2002/0182249 A1 | 12/2002 | Papahadjopoulo | |
| 2002/0187127 A1 | 12/2002 | Bankiewicz | |
| 2004/0028673 A1 | 2/2004 | Netzer et al. | |
| 2004/0209810 A1 | 10/2004 | Gill et al. | |
| 2005/0112065 A1 | 5/2005 | Drummond et al. | |
| 2005/0137134 A1 | 6/2005 | Gill et al. | |
| 2005/0180955 A1 | 8/2005 | Bankiewicz et al. | |
| 2006/0008909 A1 | 1/2006 | Cullis et al. | |
| 2006/0073101 A1 | 4/2006 | Oldfield et al. | |

FOREIGN PATENT DOCUMENTS

| | | |
|---|---|---|
| WO | WO 93/006116 | 4/1993 |
| WO | WO 2004/031348 | 4/2004 |
| WO | WO 2005/120548 | 12/2005 |
| WO | WO 2006/044115 | 4/2006 |

OTHER PUBLICATIONS

Pezet et al., Expert Opin Ther Targets, 8(5):391-399, 2004.*
Saito et al., Cancer Res, 64(7):2752-2579, 2004.*
Akerud; et al. "Differential effects of glial cell line-derived neurotrophic factor and neurturin on developing and adult substantia nigra dopamineraic neurons", Journal of Neurochemistry (1999), 73(1):70-78.
Allen; et al. "Clinical relevance of the neurotrophins and their receptors", Clinical Science (2006), 110:175-191.
Bankiewicz; et al. "Convection-enhanced delivery of AAV vector in parkinsonian monkeys; in vivo detection of gene expression and restoration of dopaminergic function using pro-drug approach",Exp Neurol (2000), 164(1):2-14.
Bankiewicz et al, Focal striatal dopamine may potentiate dyskinesias in parkinsonian monkeys. Exp Neurol (2005), 197:363-372.
Bankiewicz; et al. "Practical Aspects of the Development of ex Vivo and in Vivo Gene Therapy for Parkinson's Disease", Experimental Neurology (1997), 144:147-56.
Beck; et al. "Mesencephalic dopaminergic neurons protected by GDNF from axotomy-induced degeneration in the adult brain", Nature (1995), 373:339-341.

(Continued)

*Primary Examiner* — Daniel E Kolker
*Assistant Examiner* — Stacey N MacFarlane
(74) *Attorney, Agent, or Firm* — Bozicevic, Field & Francis LLP; Pamela J. Sherwood

(57) ABSTRACT

A method and system that is directed to the local delivery of growth factors to the mammalian CNS to treat CNS disorders associated with neuronal death and/or dysfunction is described.

20 Claims, 12 Drawing Sheets

(56) References Cited

OTHER PUBLICATIONS

Blesch; et al.,"Regulated lentiviral NGF gene transfer controls rescue of medial septal cholinergic neurons", Molecular Therapy (2005), 11:916-925.
Boado; et al. "Comparison of blood-brain barrier transport of glial-derived neurotrophic factor (GDNF) and an IgG-GDNF fusion protein in the rhesus monkey", Drug Metab Dispos (Dec. 2009), 37(12):2299-2304.
Bobo; et al. "Convection-enhanced delivery of macromolecules in the brain", PNAS (1994), 91(6):2076-2080.
Brain Activity: Academic and Research News 5(1). Neuro-Oncology Symposium: "Advances in Research and Treatment in the 21st Century" San Francisco, California, Sep. 14, 2002: CED of liposomes was first mentioned in the talk presented by Dr.
Brem; et al."Interstitial chemotherapy with drug polymer implants for the treatment of recurrent gliomas", J Neurosurg (1991), 74 (3): 441-446.
Bruce; et al. "Intracerebral clysis in a rat glioma model", Neurosurgery (2000), 46(3):683-691.
Brundin, "GDNF Treatmeant Parkinson's disease:Tim for controlled clinical trials?" Brain,Oxford (2002), 125(10):2149-2151.
Chen; et al, A realistic brain tissue phantom for intraparenchymal infusion studies. J Neurosurg (2004), 101:314-322.
Chen; et al, Combination Therapy with Irinotecan and Protein Kinase C Inhibitors in Malignant Glioma. Cancer (2003), 97(9):2363-2373.
Chen; et al, Surface properties, more than size, limiting convective distribution of virus-sized particles and viruses in the central nervous system. J. Neurosurg. (2005),103:311-19.
Chen et al, Variables affecting convection-enhanced delivery to the striatum: a systematic examination of rate of infusion, cannula size, infusate concentration, and tissue-cannula sealing time, J Neurosurg (1999), 90(2):315-20.
Choi-Lundberg; et al., "Applications of gene therapy to neurological diseases and injuries", In: Stem Cell Biology and Gene Therapy. New York, NY: Wiley-Liss, Inc. (1998), 503-505. (Summary Only).
Connor; et al. "The role of neuronal growth factors in neurodegenerative disorders of the human brain", Brain Res Brain Res Rev (1998), 27(1):1-39. (Abstract Only).
Creddon; et al., "Neurturin share receptors and signal transduction pathways with glial cell line-derived neurotrophic factor in sympathetic neurons", Proceedings of the National Academy of Sciences (1997), 94:7018-7023.
Croteau; et al., "Real-time in vivo imaging of the convective distribution of a low-molecular-weight tracer", J. Neurosurg. (Jan. 2005), 102(1):90-97.
Cunningham et al, Distribution of AAV-TK following intracranial convection-enhanced delivery into rats. Cell Transplant (2000), 9(5):585-594.
Daadi; et al. "Distribution of AAV2-hAADC-transduced cells after 3 years in Parkinsonian monkeys", Neuroreport (2006),17(2):201-204.
Dawbarn; et al, Neurotrophins and neurodegeneration. Neuropath. and App. Neurobiol (2003), 329:211-230.
Durbec; et al, "GDNF signalling through the ret receptor tyrosine kinase", Nature (1996), 381:789-793.
Eslamboli; et al, Assessment of GDNF in primate models of Parkinson's disease: Comparison with human studies. Rev Neurosci 2005;16:303-310.
Forgie; et al, Differences and developmental changes in the responsiveness of PNS neurons to GDNF and neurturin. Mol Cell Neurosci 1999;13:430-440.
Friedman; et al, The emerging role of Irinotecan (CPT-11) in the treatment of malignant glioma in brain tumors. Cancer (2003),97(9s):2359-2362.
Grondin; et al., "Chronic, Controlled GDNF Infusion Promotes Structural and Functional Recovery in Advanced Parkinsinian Monkeys," Oxford Univ. Press (2002), 125(10) 2191-2201.
Gill; et al. "Direct brain infusion of glial cell line-derived neurotrophic factor in Parkinson disease" Nat Med (2003), 9(5):589-595.
Groothuis, The blood-brain and blood-tumor barriers: a review of strategies for increasing drug delivery. Neuro-oncol (2000);2(1):45-59.
Hadaczek; et al. "Convection-enhanced delivery of adena-associated virus type 2 (AAV2) into the striatum and transport of AAV2 within monkey brain", Human Gene Therapy (2006),17:1-12.
Hadaczek; et al. "The "Perivascular Pump" driven by arterial pulsation is a powerful mechanism for the distribution of therapeutic molecules within the brain", Mol Ther (2006):14(1):69-78.
Hamilton; et al. "Heparin co infusion during convection-enhanced delivery (CEO) increases the distribution of the glial-derived neurotrophic factor (GDNF) ligand family in rat striatum and enhances the pharmacological activity of neurturin". Exp Neural (2001),168:155-161.
Haroun; et al. "Local drug delivery", Current Opinion in Oncology (2000),12:187-193.
Hefti; et al. "Neurotrophic factor therapy for neurodegenerative diseases", J Neurobiol (1994), 25:1418-1435.
Henderson; et al. "GDNF: A Potent Survival Factor for Motoneurons Present in Peripheral Nerve and Muscle", Science (1994), 266:1062-1064.
Hoane; et al."Differential in vivo effects of neurturin and glial cell-line-derived neurotrophic factor", Experimental Neurology (1999),160(1):235-243.
Hoffer; et al. "Glial cell line-derived neurotrophic factor reverses toxin-induced injury to midbrain dopaminergic neurons in vivo", Neurosci Lett (1994), 182:107-111.
Horger; et al., "Neurturin exerts potent actions on survival and function of midbrain dopaminergic neurons", The Journal of Neuroscience (1998), 18(13):4929-37.
Hudson et al, Glial cell line-derived neurotrophic factor augments midbrain dopaminergic circuits in vivo. Brain Res Bill (1995), 36:425-432.
Jackson; et al., "Comparison of Segmentation Techniques Applied to MR Images of Convectively Delivered Gadolinium-labeled Liposomes in Monkey Brains", Proceedings from the 13th Scientific meeting of the International Society of Magnetic Resonance in Medicine.
Jomary; et al., "Expression of neurturin, glial cell line-derived neurotrophic factor, and their receptor components in light-induced retinal degeneration", Invest Ophthalmol Vis Sci (2004), 45(4):1240-1246.
Kirik; et al., "Localized striatal delivery of GDNF as a treatment for Parkinson disease", Nature Neuroscience (2004), 7(2):105-110.
Kordower; et al, Clinicopathological findings following intraventricular glial-derived neurotrophic factor treatment in a patient with Parkinson's disease. Ann Neurol (1999),46:419-424.
Kordower; et al, Lentiviral gene transfer to nonhuman primate brain. Experimental Neurology (1999),160:1-16.
Kordower et al, Neurodegeneration prevented by lentiviral vector delivery of GDNF in primate models of Parkinson's disease. Science 2000;290:767-773.
Kotzbauer; et al., "Neurturin, a relative of glial-cell-line-derived neurotrophic factor", Nature (1996), 384:467-470.
Krauze; et al. "Effects of the perivascular space on convection-enhanced delivery of liposomes in primate putamen", Experimental Neurology (2005),196:104-111.
Krauze; et al. "Real-time imaging and quantification of brain delivery of liposomes", Pharmaceutical Research (2006), 23:2493-2504.
Krauze; et al. "Real-time visualization and characterization of liposomal delivery into the monkey brain by magnetic resonance imaging", Brain Res Brain Res Protoc (2005), 16(1-3):20-26.
Krauze; et al, Reflux-free cannula for convection-enhanced high-speed delivery of therapeutic agents. J Neurosurg (2005), 103:923-9.
Krauze; et al., "Pharmacokinetics, Toxicity, and Efficacy of Liposomal CPT-11 Administered by Convection-enhanced Delivery in Intracranial Brain Tumor Xenografts", Cancer Research (in Dress) 2006.
Kroll et al, Increasing volume of distribution to the brain with interstitial infusion: dose, rather than convection, might be the most important factor. Neurosurgery (1996), 38(4):746-752.

(56) References Cited

OTHER PUBLICATIONS

Lang et al, Randomized controlled trial of intraputamental glial cell line-derived neurotrophic factor infusion in Parkinson's disease. Ann Neurol (2006), 59:459-466.

Lapchak et al., "Adenoviral vector-mediated GDNF gene therapy in a rodent lesion model of late stage Parkinson's disease", Brain Research (1997), 777(1-2):153-160.

Laske et al, Chronic interstitial infusion of protein to primate brain: determination of drug distribution and clearance with single-photon emission computerized tomography imaging. J Neurosurg (1997), 87(4):586-594.

Li; et al, Experimental Neurology, (2002), 178:49-58.

Lieberman; et al. "Convection-enhanced distribution of large molecules in gray matter during interstitial drug infusion", J Neurosurg (1995), 82(6):1021-1029.

Lin; et al., "AAV2/5 Vector Expressing Galactocerebrosidase Ameliorates CNS Disease in the Murine Model of Globoid-Cell Leukodystrophy More Efficiently Than AAV2", Science (1993), 260:1130-1132.

Lonser; et al. "Successful and safe perfusion of the primate brainstem: in vivo magnetic resonance imaging of macromolecular distribution during infusion", J Neurosurg (2002), 97(4):905-913.

Love; et al. "Glial cell line-derived neurotrophic factor induces neuronal sprouting in human brain", Nat Med (2005), 11:703-704.

Mackay; et al, Distribution in brain of liposomes after convection enhanced delivery; modulation by particle charge, particle diameter, and presence of steric coating. Brain Research (2005),1035:139-153.

Mamot; et al, Extensive distribution of liposomes in rodent brains and brain tumors following convection-enhanced delivery. J Neurooncol (2004), 68(1):1-9.

Mardor; et al, Convection-enhanced drug delivery: Increased efficacy and magnetic resonance image monitoring. Cancer Research (2005), 65:6858-63.

Mardor; et al, Monitoring response to convection-enhanced taxol delivery in brain tumor patients using diffusion-weighted magnetic resonance imaging. Cancer Res (2001), 61(13):4971-3.

Martin; et al. Brain Research, 683:12-178 1995.

Masswood; et al., "Effects of chronic intraoutamneal infusion of glial cell line derived neurotrophic factor (GDNF) in aged Rhesus monkeys" Neuro of Aging (2002), 23(5) 881-889.

Morrison; et al. "Focal delivery during direct infusion to brain: role of flow rate, catheter diameter, and tissue mechanics", Am. J. Physiol. Regul. lntegr. Camp. Physiol. (1999), 277:1218-1229.

Morrison; et al. "High-flow microinfusion: tissue penetration and pharmacodynamics", Am J Physiol (1994), 266(1.2):R292-305.

Morrison; et al."Convective delivery of glial cell line-derived neurotrophic factor in the human putamen", J Neurosurg (Jul. 2007), 107(1):74-83.

Nakagawa; et al. "Dexamethasone effects on vascular volume and tissue hematocrit in experimental RG-2 gliomas and adjacent brain", J Neurooncol (1988), 6(2):157-168.

Neuwelt; et al."Mechanisms of disease: The blood-brain barrier", Neurosurgery (2004), 54:131-142.

Nguyen; et al. "Convection-enhanced delivery of AAV-2 combined with heparin increases TK gene transfer in the rat brain", Neuroreport (2001), 12(9):1961-1964.

Nguyen; et. al., "Convective distribution of macromolecules in the primate brain demonstrated using computerized tomography and magnetic resonance imaging", J. Neurosurg. (Mar. 2003), 98(3):584-90.

Nicholoson; et al., "Hindered diffusion of high molecular weight compounds in brain extracellular microenvironment measured with integrative optical imaging", Biophysical Journal (1993), 65:2277-90.

Nicholson et al, Extracellular space structure revealed by diffusion analysis. Trends Neurosci (1998), 21:207-215.

Nutt et al., "Randomized, double-blind trial of glial cell line-derived neurotrophic factor (GDNF) in PD", Neurology (2003), 60(1):69-73.

Olson, "NGF and the treatment of Alzheimer's disease", Experimental Neurology (1993),124:5-15.

Oppenheim; et al., "Developing motor neurons rescued from programmed and axotomy-induced cell death by GDNF", Nature (1995), 373: 344-346.

Pardridge, Drug Delivery to the Brain. J Cereb Blood Flow Metab (1997), 17:713-31.

Pardridge, The blood-brain barrier: Bottleneck in brain drug development. NeuroRx (2005), 2:3-14.

Patel; et al, Intraputamenal Infusion of Glial Cell Line-Derived Neurotrophic Factor in PD: A Two-Year Outcome Study. Ann Neurol (2005), 57:298-302.

Popperl; et al, O-(2[18F]flurorethyl)-L-tyrosine PET for monitoring the effects of convection-enhanced delivery of paclitaxel in patients with recurrent glioblastoma. European J. Nuclear Medicine and Mol. Imaging (2005), 32:1018-1025.

Remy; et al, Differential regulation of GDNF, neurturin, and their receptors in primary cultures of rat glial cells. J Neurosci Res (2001), 64(3):242-251.

Saito; et al, Convection-enhanced delivery of tumor necrosis factor-related apoptosis-inducing ligand with systemic administration of temozolomide prolongs survival in an intracranial glioblastoma xenograft model. Cancer Res (2004), 64(19):6858-62.

Saito; et al, Distribution of Liposomes into Brain and Rat Brain Tumor Models by Convection-Enhanced Delivery Monitored wih Magnetic Resonance Imaging. Cancer Research (2004),64:2572-9.

Saito; et al, Gadolinium-loaded liposomes allow for real-time magnetic resonance imaging of convection-enhanced delivery in the primate brain. Exp Neurol (2005), 196(2):381-389.

Saito; et al, Tissue affinity of the infusate affects the distribution volume during convection-enhanced delivery into rodent brains: Implications for local drug delivery. J Neurosci Methods (2006),154(1-2):225-232.

Saito; et al., "Convection enhanced delivery of Gadolinium-loaded liposomes into the entral nervous system of non-human primates during real-time magnetic resonance imaging", Abstracts from the Ninth Annual Meeting of the Society for Neuro-Oncology, Nov. 2004.

Saito; et al., "Convection-enhanced delivery of Ls-TPT enables an effective, continuous, low-dose chemotherapy against malignant glioma xenograft model", Neuro Oncol (2006), 8(3):205-214.

Sampson; et al, Progress report of a Phase I study of the intracerebral microinfusion of a recombinant chimeric protein composed of transforming growth factor (TGF)-alpha and a mutated form of the *Pseudomonas* exotoxin termed PE-38 (TP-38) for the treatment of malignant brain tumors. J Neuro-oncology (2003),65:27-35.

Sampson; et al., "Comparison of intratumoral bolus injection and convection-enhanced delivery of radiolabeled antitenascin monoclonal antibodies", Neurosurg. Focus (Apr. 2006), 20(4):E14.

Sanfter; et al, AAV2-mediated gene delivery to monkey putamen: evaluation of an infusion device and delivery parameters. Exp Neurol (2005), 194(2):476-483.

Slevin; et al., "Unilateral intraputamenal glial cell line-derived neurotrophic factor in patients with Parkinson disease: response to 1 year of treatment and 1 year of withdrawal", J Neurosurg (2007), 106(4):614-620.

Slevin; et al., Improvement of bilateral motor functions in patients with Parkinsons disease through the unilateral intraputaminal nfusion of glial cell line-derived neusurgery (2005), 102 (2) 216-2222.

Simonato; et., TREND in Pharmacological Sciences, (2006), 27 (12): 631-638.

Tardi; et al., "Liposomal Encapsulation of Topotecan Enhances Anti-cancer Efficacy in Murine and Human Xenograft Models", Cancer Research (2000), 60(13):3389-93.

Thoenen; et al., "Neurotrophic Factors", Science (1985), 229:238-242.

Thorne; et al, Delivery of neurotrophic factors to the central nervous system. Clin Pharmacokinet (2001),40:907-946.

Tomac; et al., "Protection and repair of the nigrostriatal dopaminergic system by GDNF in vivo", Nature (1995), 373:335-339.

Tuszynski; et al, A phase 1 clinical trial of nerve growth factor gene therapy for Alzheimer disease. Nat Med (2005),11(5):551-555.

(56) References Cited

OTHER PUBLICATIONS

Westphal; et al, Perspectives of cellular and molecular neurosurgery. J Neurooncol (2004),70(2):255-269.

Yan; et al. "In vivo neurotrophic effects of GDNF on neonatal and adult facial motor neurons", Nature (1995), 373:341-344.

Yashara; et al, "Glial cell line derived neurotrophic factor (GDNF) therapy for Parkinson's disease", Acta Medica Okayama (2007), 61(2):51-56.

Zuccato; et al. "Progressive loss of BDNF in a mouse model of Huntington's disease and rescue by BDNF delivery", Pharmacal Res (2005), 52(2):133-139.

Zuchetti; et al. "Distribution of daunorubicin and daunorubicinol in human glioma tumors after administration of liposomal daunoribucin", Cancer Chemother Pharmacol (1999), 44:173-176.

Zunkeler; et al. "Hyperosmolar blood-brain barrier disruption in baboons: an in vivo study using positron emission tomography and rubidium-82", J Neurosurg (1996), 84(3):494-502.

Zunkeler; et al., "Quantification and pharmacokinetics of blood-brain barrier disruption in humans", J Neurosurg (1996), 85(6):1056-65.

Zurn; et al, Glial cell line-derived neurotrophic factor (GDNF), a new neurotrophic factor for mononeurones. Neuroreport (1994), 6:113-118.

* cited by examiner

ADMINISTRATION OF GROWTH FACTORS FOR THE TREATMENT OF CNS DISORDERS

CROSS-REFERENCE TO RELATED APPLICATIONS

This application claims priority to U.S. provisional application Ser. No. 60/795,012, filed on Apr. 25, 2006, which is incorporated herein by reference in its entirety.

STATEMENT REGARDING FEDERALLY SPONSORED RESEARCH OR DEVELOPMENT

This invention was made with Government support under Grant No. NINDS U54 NS045309, awarded by the National Institutes of Neurological Disorders and Stroke. The U.S. Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains to neurodegenerative diseases and other conditions characterized by neuronal death and/or dysfunction in the central nervous system. The invention also concerns growth factors that are capable of promoting the survival of neurons in the central nervous system. The invention relates specifically to methods of treating neurodegenerative diseases and conditions characterized by neuronal death and/or dysfunction in the central nervous system with the local administration of growth factors.

2. Description of Related Art

Growth factors are natural proteins that play important roles in the nervous system. They are found within nervous tissue as well as in many innervated target tissues. Growth factors promote the growth, survival, and phenotypic differentiation of neurons and/or glial cells. Growth factors also play a role in the remodeling of synaptic connections in the mature nervous system, a process referred to generally as neuronal plasticity. Because of these physiological roles, growth factors are useful for treating central nervous system (CNS) disorders in which the survival and/or proper function of neurons is compromised. Such CNS disorders may arise by many different means, including: (1) physical injury, which causes the degeneration of the axonal processes and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine (ddC), respectively, (4) chronic metabolic diseases, such as diabetes or renal dysfunction, or (5) neurodegenerative diseases such as Parkinson's disease, Huntington's Disease, Alzheimer's disease, and Amyotrophic Lateral Sclerosis (ALS), which result from the degeneration of specific neuronal populations.

The therapeutic effect of a growth factor delivered to the CNS may derive from multiple mechanisms of action. Growth factors may contribute to therapeutic efficacy by promoting the survival and/or maintaining the phenotypic differentiation of a neuronal population that is compromised in a CNS disorder. Additionally, growth factors may act on secondary neuronal populations which are not compromised in a particular CNS disorder but are able to effect beneficial compensatory changes in the CNS in response to growth factor, for example, through neuronal plasticity. In order for a particular growth factor to be potentially useful in treating a CNS disorder, the neuronal population compromised in the CNS disorder or a compensating secondary neuronal population must be responsive to the particular factor. Responsiveness to a particular growth factor is conferred by its cognate growth factor receptor, the vast majority of which belong to the family of receptor tyrosine kinases.

Nerve growth factor (NGF) is the founding member of a defined family of growth factors, called the neurotrophins, that includes brain-derived neurotrophic factor (BDNF), neurotrophin-3 (NT-3), NT-4/5, and NT-6. These neurotrophins are known to act via the family of trk tyrosine kinase receptors, i.e., trkA, trkB, trkC, and the low affinity p75 receptor.

Glial cell line-derived neurotrophic factor (GDNF) is a glycosylated disulfide-bonded homodimer that has its closest structural homology to the transforming growth factor (TGF) superfamily of proteins. GDNF was identified and purified using assays based upon its efficacy in promoting the survival and stimulating the transmitter phenotype of mesencephalic dopaminergic neurons in vitro. In vivo, treatment with exogenous GDNF stimulates the dopaminergic phenotype of substantia nigra neurons, and restores functional deficits induced by axotomy or dopaminergic neurotoxins in animal models of Parkinson's disease. Although originally thought to be relatively specific for dopaminergic neurons, subsequent experiments showed that GDNF has neurotrophic efficacy on brain stem and spinal cord cholinergic neurons, both in vitro and in vivo.

GDNF, and the related ligands neurturin, artemin, and persephin, maintain several neuronal populations in the CNS, including midbrain dopamine neurons and motoneurons. The GDNF family of ligands bind to specific GDNF family receptor alpha proteins, which form receptor complexes and signal through the RET receptor tyrosine kinase. GDNF is also capable of signaling directly through alpha receptor, as well as through the neural cell adhesion molecule (NCAM) via activation of Fyn and FAK.

In the CNS, the expression of trkA, the receptor for NGF, is almost exclusively limited to the cholinergic neurons in the basal forebrain. These cholinergic neurons are of particular neurologic interest, because cholinergic neuronal degeneration and/or dystrophy is a hallmark of Alzheimer's disease. The basal forebrain cholinergic neurons can be readily identified in morphologic preparations using acetylcholinesterase histochemistry or with immunohistochemistry using antibody to choline acetyltransferase (ChAT), the synthetic enzyme for acetylcholine, or to p75.

Alzheimer's disease is a progressive dementia characterized by failure of recent memory, amnesia, disturbances in emotional behavior, and difficulty in managing spatial relationships or motor skills. The disease occurs throughout the world and accounts for one-half to two-thirds of all cases of late-life intellectual failure in many developed countries having populations with high life expectancies.

Alzheimer's disease is diagnosed mainly by clinical symptoms, after other causes of dementia have been excluded. After death, the diagnosis can be conclusively established by the observation of numerous characteristic neurofibrillary tangles and senile plaques in the brain that accompany the degeneration seen in Alzheimer's disease.

Progressive region-specific loss and degeneration of selected cells in the association and memory areas of the cerebral cortex is seen in Alzheimer's disease, along with abnormalities in certain subcortical nuclei. Neuronal loss affects especially the large pyramidal cells of the parietal and frontal association areas, the hippocampus and amygdala. Strongly affected hippocampal inputs are those from the entorhinal cortex, cholinergic neurons of the basal forebrain, and noradrenergic neurons of the locus coeruleus. The basal forebrain nucleus of Meynert, from which the major cholinergic projection to the cortex arises, also suffers severe degeneration.

Substantial evidence points to a significant role for basal forebrain cholinergic neurons in the behavioral alterations seen in Alzheimer's patients. The loss of cholinergic function is one of the earliest changes in the disease. The extent of the cholinergic deficit correlates with the degree of memory impairment, and enhancement of cholinergic function by acetylcholinesterase inhibitors produces modest but significant amelioration of symptoms. In animals, lesions of the cholinergic neurons innervating the hippocampus and cortex result in pronounced memory and cognitive deficits that are reversed by drugs that enhance cholinergic function.

Projection neurons producing other monoamine transmitters (norepinephrine, serotonin, and dopamine) and cortical neurons producing glutamate, gamma-aminobutyric acid (GABA), somatostatin, neuropeptide Y, corticotropin releasing factor, substance P and other neuromodulators are also affected in Alzheimer's disease.

While early research pointed to the promise of NGF as a therapeutic for Alzheimer's disease and other neuropathologies, untenable side effects have been observed in human clinical trials using NGF. Systemic administration of NGF at low doses for the treatment of peripheral neuropathy has caused severe muscle pain in some patients, while Alzheimer's patients treated with intracerebroventricular infusions of NGF experienced peripheral rostral muscle pain similar to that reported with peripheral NGF administration, and significant weight loss.

Clinical trials using GDNF for the treatment of Parkinson's disease have also been reported and have shown mixed results. Parkinson's disease is a disorder in which slow degeneration of dopamine-producing neurons, mostly in the nigrostriatal pathway, results in neurological effect. Intraventricular administration of GDNF did not lead to a determinable clinical benefit, and multiple adverse side effects were reported. Local delivery of GDNF to the striatum has also been used to treat Parkinson's disease. Two clinical trials involving the continuous infusion and diffusion of GDNF into the dorsal putamen reported different results, potentially owing at least in part to differences in dosage and delivery.

Importantly, neutralizing anti-GDNF antibodies were detected in sera from several human patients, and in a toxicology study, segmental cerebellar injury characterized by Purkinje and granule cell loss was observed in monkeys receiving GDNF infusion.

Clinical studies involving neurotrophin infusion into the brain parenchyma of patients with neurodegenerative disease have used continuous infusion and relied on diffusion for infusate to reach target tissues. There are a number of difficulties associated with diffusion-based delivery, the most critical being low tissue distribution volume. Without means for monitoring the distribution of infused neurotrophin, it is difficult to determine the therapeutic efficacy. For example, Gill et al. reported in Nat. Med. 9:5899-595, 2003 that, when glial cell line-derived neurotrophic factor (GDNF) was used in clinical studies as a treatment for Parkinson's disease, it was not clear how far GDNF would diffuse away from the catheter tip and that it is possible more rostral portions of the putamen would continue to degenerate if not reached by diffusion. They also found that, as the dose of GDNF was escalated, a high T2 MRI signal intensity was observed around the tip of the catheter, possibly owing to vasogenic edema or protein buildup, which required dosage reduction and potentially further compromised rostral portions of the putamen.

There continues to exist a need for methods and therapeutic compositions useful for the treatment of CNS disorders, including neurodegenerative diseases such as Alzheimer's disease and Parkinson's disease.

SUMMARY OF INVENTION

The invention stems in part from the discovery that the tissue clearance rate of growth factors in mammalian CNS tissue is lower than previously believed. In particular, the present disclosure establishes that growth factors infused into the brain parenchyma in a typical treatment regimen are detectable for up to about 2-6 weeks post delivery.

Previous trials involving growth factor infusion into the brain parenchyma for the treatment of neurodegenerative disease have employed continuous infusion. However, as a consequence of remarkably low tissue clearance rates, continuous infusion of growth factor is unnecessary to achieve a therapeutically effective level of growth factor in targeted brain tissue, and the accumulation that results from continuous administration can have adverse effects. For example, accumulation of growth factor in brain parenchyma can lead to dose build-up and leakage to secondary sites and CSF, which has the potential to cause undesirable secondary effects as well as immune responses and attendant production of growth factor neutralizing antibodies. Such neutralizing anti-GDNF antibodies have been observed in the sera of patients receiving continuous infusion of GDNF into the striatum. Additionally, cellular toxicity has been observed at secondary sites in a GDNF animal toxicity study, and flow of infusate from the putamen to secondary sites via the perivascular space has been observed in primates.

The present invention is directed to achieving and maintaining an effective therapeutic dose of growth factor in targeted CNS tissue while avoiding dose build-up leading to overdose to reduce the risk of adverse events, including the production of neutralizing antibodies and the initiation of an immune response. The invention achieves these objectives with growth factor administration regimens that counterbalance previously unrecognized tissue clearance rates in order to provide for a sustained effective therapeutic dose of growth factor in compromised CNS tissue. In contrast, prior art efforts to regulate the therapeutic dosage of growth factors employed sensors capable of detecting electrical activity indicative of neuronal degeneration or dysfunction, Elsberry et al., U.S. Pat. No. 6,042,579; an inadequate feedback parameter that fails to address adverse events such as the immune-mediated processes noted above.

In a preferred embodiment, the administration regimen involves intermittent delivery, wherein delivery counterbalances tissue clearance.

In a preferred embodiment, the invention involves the method of convection enhanced delivery ("CED"), preferably in conjunction with a step-design reflux-free cannula for the delivery of growth factor to compromised cell populations in the CNS. In a preferred embodiment, the invention further involves the delivery of a tracing agent with the growth factor, and the tracing agent acts as a surrogate for monitoring distribution of infused growth factor. In a preferred embodiment, the invention further involves the use of a facilitating agent, which provides for increased growth factor mobility in brain parenchyma. Thus, in addition to addressing the problems associated with growth factor accumulation, the present invention overcomes the limitations inherent in diffusion-based delivery with typical catheters, particularly low tissue distribution volume, accumulation at catheter tip, reflux, and leakage to secondary sites and CSF, and provides for the real-time monitoring and optimization of neurotherapeutic administration.

In accordance with the objectives stated above, in one aspect, the invention provides methods for promoting the survival of a growth factor-responsive neuronal population in the mammalian CNS. The methods comprise locally delivering a pharmaceutical composition comprising a growth factor to the growth factor-responsive neuronal population, wherein the growth factor is delivered at a rate that substantially opposes the tissue clearance rate of the growth factor, whereby a therapeutically effective amount of growth factor is achieved in the target CNS tissue. Such an administration regimen is designed to avoid substantial accumulation of growth factor.

In one embodiment, the method comprises the step of determining the clearance rate of the growth factor that is to be locally delivered to a growth factor-responsive neuronal population in the CNS. In a preferred embodiment, the clearance rate determining step is done preclinically, preferably in a primate. In another preferred embodiment, the clearance rate determining step is done by measurement of a clearance rate indicator in a human subject.

In a preferred embodiment, the pharmaceutical composition is deliverable by convection enhanced delivery (CED).

In a preferred embodiment, the pharmaceutical composition is delivered locally by CED.

In a preferred embodiment, CED comprises an infusion rate of between about 0.5 μL/min and about 10 μL/min.

In a preferred embodiment, CED comprises an infusion rate of greater than about 0.5 μL/min, more preferably greater than about 0.7 μL/min, more preferably greater than about 1 μL/min, more preferably greater than about 1.2 μL/min, more preferably greater than about 1.5 μL/min, more preferably greater than about 1.7 μL/min, more preferably greater than about 2 μL/min, more preferably greater than about 2.2 μL/min, more preferably greater than about 2.5 μL/min, more preferably greater than about 2.7 μL/min, more preferably greater than about 3 μL/min, as well as preferably less than about 25 μL/min, more preferably less than 20 μL/min, more preferably less than about 15 μL/min, more preferably less than about 12 μL/min, more preferably less than about 10 μL/min.

In a preferred embodiment, CED comprises incremental increases in flow rate, referred to as "stepping", during delivery. Preferably, stepping comprises infusion rates of between about 0.5 μL/min and about 10 μL/min.

In a preferred embodiment, stepping comprises infusion rates of greater than about 0.5 μL/min, more preferably greater than about 0.7 μL/min, more preferably greater than about 1 μL/min, more preferably greater than about 1.2 μL/min, more preferably greater than about 1.5 μL/min, more preferably greater than about 1.7 μL/min, more preferably greater than about 2 μL/min, more preferably greater than about 2.2 μL/min, more preferably greater than about 2.5 μL/min, more preferably greater than about 2.7 μL/min, more preferably greater than about 3 μL/min, as well as preferably less than about 25 μL/min, more preferably less than 20 μL/min, more preferably less than about 15 μL/min, more preferably less than about 12 μL/min, more preferably less than about 10 μL/min.

In a preferred embodiment, the pharmaceutical composition is delivered with the use of a CED-compatible reflux-free step-design cannula.

In one embodiment, the step-design cannula is compatible with chronic administration. Such cannulas are preferred for use in the treatment of chronic CNS disorders, as described herein.

In another embodiment, the step-design cannula is compatible with acute administration. Such cannulas are preferred for use in the treatment of acute CNS disorders, as described herein.

In a preferred embodiment, the pharmaceutical composition comprises a tracing agent that provides for guided growth factor delivery. Preferably, the tracing agent is an MRI contrast agent, sometimes referred to herein as an "MRI magnet". In a preferred embodiment, the tracing agent comprises a liposome. In an especially preferred embodiment, the tracing agent comprises a liposome containing gadolinium chelate.

In a preferred embodiment, the pharmaceutical composition comprises a facilitating agent, which facilitates delivery of growth factor to target tissue. In a preferred embodiment, the facilitating agent is low molecular weight heparin.

In one embodiment, the pharmaceutical composition comprises a high molecular weight neurotherapeutic comprising a growth factor and a carrier. In one embodiment, the carrier is a synthetic carrier. A wide variety of synthetic carriers are available for use in the high molecular weight neurotherapeutics of the invention. In a preferred embodiment, the carrier is a liposome. In another preferred embodiment, the carrier is a metal particle, such as a gold particle, or a polymer. In another embodiment, the carrier is a naturally occurring composition or variant thereof. Examples of such natural carriers include virus particles, including modified virus particles (e.g., those having a modified surface protein profile).

In a preferred embodiment, the pharmaceutical composition comprises a growth factor that is selected from the group consisting of NGF, BDNF, NT-3, NT-4/5, NT-6, GDNF, CNTF, LIF, IGF-1, b-FGF, neurturin, persephin, artemin, TGFα, TGFβ, IGF-2, PDGF, EGF, cardiotropin, EGF, IGF, VEGF, Sonic hedgehog (SHH), BMP, FGF20, VIP, PDGF, pleiotrophin (PTN), and HGF.

In one embodiment, the pharmaceutical composition comprises a nucleic acid encoding a growth factor. In a preferred embodiment, the growth factor is selected from the group consisting of NGF, BDNF, NT-3, NT-4/5, NT-6, GDNF, CNTF, LIF, IGF-1, b-FGF, neurturin, persephin, artemin, TGFα, TGFβ, IGF-2, PDGF, EGF, cardiotropin, EGF, IGF, VEGF, Sonic hedgehog (SHH), BMP, FGF20, VIP, PDGF, pleiotrophin (PTN), and HGF. In a preferred embodiment, the pharmaceutical composition comprises a vector, which vector comprises such a nucleic acid encoding a growth factor under the control of a regulatable promoter.

In a preferred embodiment, the pharmaceutical composition comprises NGF, or an active fragment or variant thereof, and the growth factor-responsive neuronal population comprises cholinergic neurons of the basal forebrain.

In a preferred embodiment, in addition to NGF, the pharmaceutical composition additionally comprises a bioactive agent selected from the group consisting of cholinergic agonists, cholinesterase inhibitor such as tacrine hydrochloride, neurotrophins, inducers of endogenous neurotrophic factor synthesis or production, inhibitors of senile amyloid plaque formation, and inhibitors of PHF formation.

In another preferred embodiment, the pharmaceutical composition comprises GDNF, or an active fragment or variant thereof, and the growth factor-responsive neuronal population comprises cholinergic neurons of the basal forebrain.

In another preferred embodiment, the pharmaceutical composition comprises GDNF, or an active fragment or variant thereof, and the growth factor-responsive neuronal population comprises dopaminergic neurons having cell bodies or processes in the striatum and/or midbrain.

In another preferred embodiment, the pharmaceutical composition comprises VIP, or an active fragment or variant thereof, and the growth factor-responsive neuronal population comprises dopaminergic neurons having cell bodies or processes in the striatum and/or midbrain.

In another preferred embodiment, the pharmaceutical composition comprises PTN, or an active fragment or variant thereof, and the growth factor-responsive neuronal population comprises dopaminergic neurons having cell bodies or processes in the striatum and/or midbrain.

It will be appreciated that in some embodiments, growth factors may be delivered to neuronal terminals at a distance from cell bodies.

In another preferred embodiment, the pharmaceutical composition comprises BMP, or an active fragment or variant thereof, and the growth factor-responsive neuronal population comprises cells of a CNS locus impacted by stroke.

In a preferred embodiment, the method comprises intermittent local delivery of the pharmaceutical composition.

In a preferred embodiment, administration of the growth factor comprises an intermission of from about 7 days to about 45 days, more preferably from about 14 days to about 45 days, more preferably from about 17 days to about 35 days, more preferably from about 20 days to about 35 days following delivery of the growth factor, which intermission is followed by another delivery of the growth factor. In a preferred embodiment, administration of the growth factor comprises two or more such intermissions.

In another embodiment, administration of the growth factor comprises intermissions of less than 7 days, preferably between about 2 days and about 6 days, or more than 45 days.

In a preferred embodiment, the duration of two or more intermissions is different in an intermittent administration regimen comprising three or more delivery steps. In a preferred embodiment, the duration of an intermission between delivery steps at the beginning of an intermittent administration regimen is substantially shorter that an intermission between subsequent delivery steps.

In one embodiment, the dose of growth factor delivered differs between delivery steps. In a preferred embodiment, the dose of growth factor delivered in an earlier delivery step is higher than the dose of growth factor delivered in a later delivery step in an intermittent administration regimen comprising two or more delivery steps.

In a preferred embodiment, the duration of CED is from about 30 minutes to about 12 hours, more preferably from about 30 minutes to about 6 hours.

In another embodiment, duration of CED is less than about 30 minutes or more than about 12 hours.

In a preferred embodiment, the duration of delivery is informed by use of a tracing agent and monitoring of infusate distribution.

In one aspect, the invention provides methods for reducing the death of growth factor-responsive neurons of the mammalian CNS. The methods comprise locally delivering a pharmaceutical composition comprising a growth factor to a growth factor-responsive CNS neuronal population that is at risk of undergoing cell death in the absence of intervention, wherein the growth factor is delivered at a rate that substantially opposes the tissue clearance rate of the growth factor, whereby a therapeutically effective amount of growth factor is achieved in the target CNS tissue.

In one aspect, the invention provides methods for modulating synapse formation by growth factor-responsive neurons of the mammalian CNS. The methods comprise locally delivering a pharmaceutical composition comprising a growth factor to a growth factor-responsive CNS neuronal population, wherein the growth factor is delivered at a rate that substantially opposes the tissue clearance rate of the growth factor, whereby a therapeutically effective amount of growth factor is achieved in the target CNS tissue, and wherein the growth factor modulates synapse formation by the growth factor-responsive neuronal population.

In one aspect, the invention provides methods for modulating neurite outgrowth by growth factor-responsive neurons of the mammalian CNS. The methods comprise locally delivering a pharmaceutical composition comprising a growth factor to a growth factor-responsive CNS neuronal population, wherein the growth factor is delivered at a rate that substantially opposes the tissue clearance rate of the growth factor, whereby a therapeutically effective amount of growth factor is achieved in the target CNS tissue, and wherein the growth factor modulates neurite outgrowth by the growth factor-responsive neuronal population.

In one aspect, the invention provides methods for increasing neurotransmitter turnover in growth factor-responsive neurons of the mammalian CNS. The methods comprise locally delivering a pharmaceutical composition comprising a growth factor to a growth factor-responsive CNS neuronal population, wherein the growth factor is delivered at a rate that substantially opposes the tissue clearance rate of the growth factor, whereby a therapeutically effective amount of growth factor is achieved in the target CNS tissue, and wherein the growth factor increases neurotransmitter turnover in the growth factor-responsive neuronal population.

In one aspect, the invention provides methods for modulating phenotypic differentiation of growth factor-responsive neurons of the mammalian CNS. The methods comprise locally delivering a pharmaceutical composition comprising a growth factor to a growth factor-responsive CNS neuronal population, wherein the growth factor is delivered at a rate that substantially opposes the tissue clearance rate of the growth factor, whereby a therapeutically effective amount of growth factor is achieved in the target CNS tissue, and wherein the growth factor modulates phenotypic differentiation of the growth factor-responsive neuronal population.

In one aspect, the invention provides methods for treating a patient having a CNS disorder characterized by neuronal death and/or dysfunction. In one embodiment, the CNS disorder is a chronic disorder. In another embodiment, the CNS disorder is an acute disorder. In a preferred embodiment, the CNS disorder is selected from the group consisting of Huntington's disease, Alzheimer's disease, amyotrophic lateral sclerosis (ALS), Parkinson's disease, stroke, head trauma, spinal cord injury, multiple sclerosis, dementia with Lewy Bodies, retinal degeneration, epilepsy, psychiatric disorders, disorders of hormonal balance, and cochlear degeneration. Further contemplated are methods for reducing inflammation that is associated with a CNS disorder characterized by neuronal death and/or dysfunction.

The methods comprise locally delivering a pharmaceutical composition comprising a growth factor to a growth factor-responsive CNS neuronal population in the patient, wherein such administration of the growth factor is therapeutically effective in the treatment of the patient. The growth factor is delivered at a rate that substantially opposes the tissue clearance rate of the growth factor, whereby a therapeutically effective amount of growth factor is achieved in the target CNS tissue.

In embodiments wherein an acute CNS disorder is treated, there is preferably an endpoint at which administration is discontinued.

In one aspect, the invention provides methods for treating a patient diagnosed as having a CNS disorder in its early stages, preferably prior to clinical presentation. The methods comprise locally delivering a pharmaceutical composition comprising a growth factor to a growth factor-responsive CNS neuronal population in the patient, wherein such administration of the growth factor prevents, delays, or reduces the severity of clinical manifestations associated with the CNS disorder. The growth factor is delivered at a rate that substantially opposes the tissue clearance rate of the growth factor, whereby a therapeutically effective amount of growth factor is achieved in the target CNS tissue.

In one aspect, the invention provides prophylactic methods for treating a patient at risk for a CNS disorder. The methods comprise locally delivering a pharmaceutical composition comprising a growth factor to a growth factor-responsive CNS neuronal population in the patient, wherein such administration of the growth factor prevents or delays onset of a CNS disorder, or reduces the severity of the CNS disorder once it is manifest. The growth factor is delivered at a rate that substantially opposes the tissue clearance rate of the growth factor, whereby a therapeutically effective amount of growth factor is achieved in the target CNS tissue.

Treatment methods including prophylactic methods herein preferably involve preoperative diagnosis.

In a preferred embodiment, preoperative diagnosis involves genetic screening. In another preferred embodiment, preoperative diagnosis involves neuroimaging. In one embodiment, the neuroimaging performed comprises functional neuroimaging. In another embodiment, the neuroimaging performed involves non-functional imaging. Preferably, the neuroimaging done involves PET, MRI, and/or CT.

Treatment methods herein also preferably comprise neuroimaging, preferably MRI, for target localization and/or guided cannula placement. Preferably a stereotactic holder is used in conjunction with neuroimaging to provide for guided cannula placement at or proximal to a target neuronal population.

Treatment methods herein also preferably comprise neuroimaging, preferably MRI in conjunction with an administered MRI magnet for monitoring infusate distribution.

In one aspect, the invention provides locally deliverable pharmaceutical compositions useful for treating a CNS disorder characterized by the death and/or dysfunction of a CNS neuronal population.

In a preferred embodiment, the pharmaceutical composition is deliverable by CED.

In a preferred embodiment, the pharmaceutical composition comprises a tracing agent.

In a preferred embodiment, the tracing agent is an MRI magnet.

In a preferred embodiment, the tracing agent comprises a liposome. In an especially preferred embodiment, the tracing agent comprises a liposome containing an MRI magnet, preferably gadolinium chelate. In a highly preferred embodiment, the tracing agent consists essentially of a liposome containing an MRI magnet, preferably gadolinium chelate.

In a preferred embodiment, the pharmaceutical composition comprises a facilitating agent.

In a preferred embodiment, the facilitating agent is low molecular weight heparin.

In a preferred embodiment, growth factor is selected from the group consisting of NGF, BDNF, NT-3, NT-4/5, NT-6, GDNF, CNTF, LIF, IGF-1, b-FGF, neurturin, persephin, artemin, TGFa, TGFb, IGF-2, PDGF, EGF, cardiotropin, EGF, IGF, VEGF, Sonic hedgehog (SHH), BMP, FGF20, VIP, PDGF, pleiotrophin (PTN), and HGF.

Methods of producing a pharmaceutical composition of the invention are also provided.

In one aspect, the invention provides a delivery device comprising a pharmaceutical composition of the invention.

In one aspect, the invention provides a catheter or cannula comprising a pharmaceutical composition of the invention.

In one aspect, the invention provides a delivery device comprising a pump that is capable of effecting delivery of a pharmaceutical composition of the invention by CED. In a preferred embodiment, the invention provides a delivery device comprising a pump that is capable of effecting intermittent delivery of a pharmaceutical composition of the invention by CED. In a preferred embodiment, the device further comprises a pharmaceutical composition of the invention. In a preferred embodiment, the device further comprises a CED-compatible, reflux-free step-design cannula, which cannula is compatible with chronic or acute administration.

In one aspect, the invention provides methods of using a growth factor or nucleic acid encoding the same to produce a medicament useful for the treatment of a patient having a CNS disorder characterized by neuronal death and/or dysfunction, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for reducing the death of growth factor-responsive neurons of the mammalian CNS, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for modulating neurite outgrowth by growth factor-responsive neurons of the mammalian CNS, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for increasing neurotransmitter turnover in growth factor-responsive neurons of the mammalian CNS, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for modulating phenotypic differentiation of growth factor-responsive neurons of the mammalian CNS, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for treating a patient diagnosed as having a CNS disorder in its early stages, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one aspect, the invention provides methods of using a growth factor or nucleic acid encoding the same to produce a medicament useful for prophylactic treatment a patient at risk for a CNS disorder, wherein the medicament is deliverable to the CNS of the patient having a CNS disorder at a rate that substantially opposes the tissue clearance rate of the growth factor, wherein the growth factor or nucleic acid encoding the same is present in an amount sufficient to provide a therapeutically effective dose when the medicament is delivered to the CNS of the patient without producing substantial accumulation of the growth factor in the CNS of the patient. In a preferred embodiment, the medicament is deliverable by CED. In a preferred embodiment, the medicament may be delivered intermittently.

In one embodiment, a medicament further comprises a tracing agent.

In one embodiment, a medicament further comprises a facilitating agent.

In one embodiment, methods of producing a medicament involve the use of a high molecular weight neurotherapeutic of the invention comprising (i) a carrier, and (ii) a growth factor or nucleic acid encoding the same.

In one aspect, the invention provides kits for the treatment of CNS disorders, which kits comprise one or more pharmaceutical compositions of the invention.

In another aspect the invention provides kits useful for reducing the death of growth factor-responsive neurons of the mammalian CNS, which kits comprise one or more pharmaceutical compositions of the invention.

In another aspect the invention provides kits useful for modulating neurite outgrowth by growth factor-responsive neurons of the mammalian CNS, which kits comprise one or more pharmaceutical compositions of the invention.

In another aspect the invention provides kits useful for increasing neurotransmitter turnover in growth factor-responsive neurons of the mammalian CNS, which kits comprise one or more pharmaceutical compositions of the invention.

In another aspect the invention provides kits useful for modulating phenotypic differentiation of growth factor-responsive neurons of the mammalian CNS, which kits comprise one or more pharmaceutical compositions of the invention.

In another aspect the invention provides kits useful for treating a patient diagnosed as having a CNS disorder in its early stages, which kits comprise one or more pharmaceutical compositions of the invention.

In another aspect the invention provides kits useful for prophylactic treatment a patient at risk for a CNS disorder, which kits comprise one or more pharmaceutical compositions of the invention.

In one embodiment, a kit of the invention further comprises a delivery device useful for CED, preferably a cannula, and more preferably a step-design reflux-free cannula. In one embodiment, a kit of the invention further comprises a pump useful for CED.

Another aspect of the invention is a method of treating a mammal having a central nervous system (CNS) disorder. In one embodiment, the method involves administering to a mammal having a CNS disorder, a pharmaceutical composition such as a growth factor, by correlating delivery of said pharmaceutical composition with corresponding tissue clearance of the pharmaceutical composition. In one embodiment, the pharmaceutical composition is administered using convection enhanced delivery (CED). In one embodiment, the pharmaceutical composition includes a tracing agent. In another embodiment, the pharmaceutical composition further comprises a facilitating agent. In one embodiment, the pharmaceutical composition is delivered intermittently. In one mode, the intermittent delivery balances the process of tissue clearance.

Another aspect of the invention is a method for promoting the survival of a growth factor-responsive neuronal population in the mammalian CNS. In one embodiment, the method involves locally delivering a pharmaceutical composition comprising a growth factor to the growth factor-responsive neuronal population wherein the growth factor is delivered at a rate that substantially opposes the tissue clearance rate of the growth factor such that a therapeutically effective amount of growth factor is achieved in the target CNS tissue. In one mode, the delivery does not produce substantial accumulation of growth factor. In one embodiment, the method as involves determining the tissue clearance rate of the growth factor that is to be locally delivered to a growth factor-responsive neuronal population in the CNS. In one embodiment, determining the tissue clearance rate is performed preclinically in a primate. In another embodiment, determining the tissue clearance rate is carried out by measuring a clearance rate indicator in a human subject.

Another aspect of the invention is a method for reducing the death of growth factor-responsive neurons of the mammalian CNS. In one embodiment, the method involves locally delivering a pharmaceutical composition comprising a growth factor to a growth factor-responsive CNS neuronal population that is at risk of undergoing cell death in the absence of intervention, wherein the growth factor is delivered at a rate that substantially opposes the tissue clearance rate of the growth factor and whereby a therapeutically effective amount of growth factor is achieved in the target CNS tissue.

Another aspect of the invention is a method of treating a CNS disorder. In one embodiment, the method involves locally administering a pharmaceutical composition comprising a growth factor to a growth factor-responsive CNS neuronal population in the patient, wherein such administration of the growth factor is therapeutically effective in the treatment of the patient. In one embodiment, the growth factor is delivered at a rate that substantially opposes the tissue clearance rate of the growth factor whereby a therapeutically effective amount of growth factor is achieved in the target CNS tissue. In one embodiment, the CNS disorder comprises an acute CNS disorder and administration is discontinued at an endpoint.

Another aspect of the invention is a method for treating a patient diagnosed as having a CNS disorder in its early stages. In one embodiment, the method involves locally administering a pharmaceutical composition comprising a growth factor to a growth factor-responsive CNS neuronal population in the patient wherein such administration of the growth factor prevents, delays, or reduces the severity of clinical manifestations associated with the CNS disorder at later stages in the absence of administered growth factor. In one embodiment, the growth factor is delivered at a rate that substantially opposes the tissue clearance rate of the growth factor whereby a therapeutically effective amount of growth factor is achieved in the target CNS tissue.

Another aspect of the invention is a prophylactic method for treating a patient at risk for a CNS disorder. In one embodiment, the method involves locally administering a pharmaceutical composition comprising a growth factor to a growth factor-responsive CNS neuronal population in the patient wherein such administration of the growth factor prevents or delays onset of a CNS disorder, or reduces the severity of the CNS disorder once it is manifest. In one embodiment, the growth factor is delivered at a rate that substantially opposes the tissue clearance rate of the growth factor whereby a therapeutically effective amount of growth factor is achieved in the target CNS tissue.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF INVENTION

Figure 1:
FIG. 1 and FIG. 2 are rat brain images. LMW Hep (1 microgram/microliter) with GDNF is infused into rat brain. (left hemisphere infused with GDNF+LMW Hep; the right hemisphere received only GDNF with PBS as a control).

The invention is directed to methods and compositions for the local delivery of growth factors to growth factor-responsive neuronal populations of the mammalian CNS. The invention stems in part from the discovery that tissue clearance of growth factors in the CNS is slow relative to rates at which exogenous growth factors have typically been administered previously. Infusion of a growth factor at a rate greater than tissue clearance results in an unnecessary and potentially toxic accumulation of growth factor. In the present invention, delivery of growth factor at a rate that substantially opposes the tissue clearance rate is done to avoid toxic accumulation of growth factor and achieve levels in target tissue that are maintained within a therapeutically effective window over time. In a preferred embodiment, intermittent growth factor delivery is done.

The phenomenon of slow tissue clearance is not limited to a particular growth factor or brain region. Consequently, the benefit associated with the present administration methods is not limited to a particular growth factor, a particular neuronal population in the CNS, or a particular indication. In principle, given the ability to deliver a wide variety of growth factors to a wide variety of neuronal populations in the CNS, any indication characterized by the death and/or dysfunction of a neuronal population that is responsive to growth factor, or may be functionally compensated for by a neuronal population responsive to growth factor, may be treated.

Administration of Growth Factor

A number of growth factors have been delivered by various means in attempts to treat a variety of neurodegenerative diseases. For review, see for example, Dawbarn et al., Neuropathol and App. Neurobiol, 29:211-230, 2003 incorporated herein by reference in its entirety. The present invention provides novel means of delivering growth factors to growth factor-responsive neuronal populations in these diseases with improved efficacy. In particular, the invention provides methods and compositions for delivering growth factors to target neuronal populations at a rate that counterbalances tissue clearance rates to achieve a sustained effective therapeutic dose without unwanted adverse effects.

In the methods of the invention, growth factor is delivered at a rate that substantially opposes the tissue clearance rate of the growth factor. By "rate that substantially opposes the tissue clearance rate" is meant a delivery rate that is approximately counter to the tissue clearance rate. Rate refers to amount of growth factor over time. The delivery rate need not exactly counter the tissue clearance rate, and the amount of growth factor in target tissue need not remain constant. For example, in a preferred embodiment of the invention, administration involves intermittent delivery of growth factor. It will be appreciated that such administration protocols will result in varied amounts of growth factor in target tissue, with a maxima approximately at the beginning of an intermission and a minima approximately at the end of an intermission. What is called for in the present methods is a delivery rate that provides for maintenance of a therapeutically effective amount of growth factor (within a therapeutic window) in target tissue over time. By considering the empirically determined clearance rate of a particular growth factor in target tissue, one of skill in the art can readily determine an appropriate delivery rate without undue experimentation.

The rate of growth factor delivery in the present methods is informed by the rate of tissue clearance of the growth factor and substantially opposes the rate of tissue clearance. The desired rate of growth factor delivery may be achieved with continuous or intermittent delivery and appropriate concentrations of growth factor. CED is preferred as a means of delivery in the present invention, and intermittent delivery of a pharmaceutical composition having an appropriate concentration of growth factor is preferred. However, in alternative embodiments, delivery at an infusion rate of less than 0.5 µl/min may be done, and an administration regimen comprising intermittent delivery with very short intermissions (days, hours, minutes), and even continuous delivery may be done with appropriate concentrations of growth factor such that the rate of delivery substantially opposes the rate of tissue clearance.

By "substantial accumulation" or "harmful accumulation" of growth factor is meant achievement of an amount of growth factor that is higher than the minimum therapeutically effective amount of growth factor and capable of producing undesirable deleterious effects, which is typically well above the maximally effective therapeutic amount of growth factor (i.e., higher than the effective ceiling amount of growth factor) for a period of time. By "intermittent delivery" is meant discontinuous delivery. In accordance with the invention, in a preferred embodiment, a particular growth factor is administered as its level in target tissue is declining in order to maintain a therapeutically effective amount of the factor in target tissue. The growth factor is infused into the target population for a period of time, typically from about 30 minutes to about 12 hours, more preferably from about 30 minutes to about 6 hours, at which point delivery ceases. The duration of delivery will be informed by a tracing agent in preferred embodiments. During delivery, the level of growth factor in the target tissue increases. Preferably, cessation of delivery occurs when the maximally effective therapeutic dose (therapeutic dosage ceiling) is achieved in target tissue. Though less preferred, cessation of delivery may occur when maximally effective therapeutic dose has been surpassed. Preferably, cessation of delivery occurs when infusate is distributed throughout the substantial whole of the target tissue, as may be monitored with a tracing agent as disclosed herein. Preferably, cessation of delivery occurs while infusate remains substantially confined to target tissue. Following cessation, tissue clearance mechanisms act to slowly decrease the level of growth factor in the target tissue. Delivery is repeated when the growth factor in target tissue is declining, preferably while a therapeutically effective amount of growth factor remains in target tissue, more preferably when the growth factor is above or slightly above the minimum therapeutically effective amount of growth factor. Though less preferred, delivery may be repeated when the growth factor is below the minimum therapeutically effective amount of growth factor. In one embodiment, a therapeutically effective dose is not maintained continuously without interruption.

In a preferred embodiment, administration of the growth factor comprises an intermission of from about 7 days to about 45 days, more preferably from about 14 days to about 45 days, more preferably from about 17 days to about 35 days, more preferably from about 20 days to about 35 days following delivery of the growth factor, which intermission is followed by another delivery of the growth factor. In a preferred embodiment, administration of the growth factor comprises two or more such intermissions.

In another embodiment, administration of the growth factor comprises intermissions of less than about 7 days or more than about 45 days.

In the methods herein, growth factors are locally delivered to a target population of growth factor-responsive neurons in the mammalian CNS by infusion. Especially preferred is the method of CED. By "CED" is meant infusion at a rate greater than 0.50/min. In a preferred embodiment, growth factor is delivered by CED through a suitable catheter or cannula, preferably a step-design reflux-free cannula. In a preferred embodiment, the method of CED is done with a CED-compatible reflux-free step design cannula. See Krauze et al., J. Neurosurg., 103:923-929, 2005, incorporated herein by reference in its entirety. See also, U.S. Patent Application Publication No. 2007/0088295 A1 and 2006/0135945 A1, both of which are incorporated herein by reference in their entirety. The method involves positioning the tip of the cannula at least in close proximity to the target tissue. After the cannula is positioned, it is connected to a pump which delivers the growth factor through the cannula tip to the target tissue. A pressure gradient from the tip of the cannula is maintained during infusion.

By "proximal to" a target population is meant within an effective distance of the target population. In particular, with respect to the positioning of a cannula relative to target tissue, proximity refers to a distance such that infusate will reach the target tissue. As the highly preferred means of delivering a pharmaceutical composition is CED, proximity in most instances herein refers to being within a distance from target tissue that is reached by CED of pharmaceutical composition.

In a preferred embodiment, a step-design reflux-free cannula is joined with a pump that withdraws the growth factor from a container and produces enough pressure to cause the growth factor to flow through the catheter to the target tissue at controlled rates. Any suitable flow rate can be used such that the intracranial pressure is maintained at suitable levels so as not to injure the brain tissue. More than a single cannula can be used.

Penetration of the growth factor into target tissue is greatly facilitated by positive pressure infusion over a period of hours. Penetration is further augmented by the use of a facilitating agent, such as low molecular weight heparin. Additionally, the inclusion of a tracing agent, preferably an MRI magnet, provides for real-time monitoring of tissue penetration by infusate, and informs the cessation of delivery.

Any suitable amount of growth factor can be administered in this manner. Suitable amounts are amounts that are therapeutically effective, and thus capable of provoking a response from growth factor responsive neurons in target tissue, without causing an overabundance of undesirable side effects. Typically, the amount of growth factor will be between about 1 µg and about 1000 µg, more preferably between about 1 µg and about 500 µg, more preferably between about 1 µg and about 250 µg, more preferably between about 1 µg and about 100 µg. In an especially preferred embodiment, the amount of growth factor is between about 10 µg and about 100 µg. In a preferred embodiment, CED comprises an infusion rate of between about 0.5 µL/min and about 10 µL/min.

In a preferred embodiment, CED comprises an infusion rate of greater than about 0.5 µL/min, more preferably greater than about 0.7 µL/min, more preferably greater than about 1 µL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, more preferably greater than about 3 µL/min, as well as preferably less than about 25 µL/min, more preferably less than 20 µL/min, more preferably less than about 15 µL/min, more preferably less than about 12 µL/min, more preferably less than about 10 µL/min.

In a preferred embodiment, CED comprises incremental increases in flow rate, referred to as "stepping", during delivery. Preferably, stepping comprises infusion rates of between about 0.5 µL/min and about 10 µL/min.

In a preferred embodiment, stepping comprises infusion rates of greater than about 0.5 µL/min, more preferably greater than about 0.7 µL/min, more preferably greater than about 1 µL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, more preferably greater than about 3 µL/min, as well as preferably less than about 25 µL/min, more preferably less than 20 µL/min, more preferably less than about 15 µL/min, more preferably less than about 12 µL/min, more preferably less than about 10 µL/min.

For further teaching on the method of CED, see for example Saito et al., Exp. Neurol., 196:3891-389, 2005; Krauze et al., Exp. Neurol., 196:104-111, 2005; Krauze et al., Brain Res. Brain Res. Protocol., 16:20-26, 2005; U.S. Patent Application Publication No. 2006/0073101; U.S. Pat. No. 5,720,720, each of which is incorporated herein by reference in its entirety.

The present methods of treatment preferably involve one or more pre-operative diagnostic determinations for the presence or risk of a CNS disorder. "CNS disorder" as used herein refers to disorders of the mammalian CNS characterized by the death and/or dysfunction of one or more neuronal populations. CNS disorders include chronic disorders, such as neurodegenerative diseases, for example Alzheimer's disease, as well as acute disorders, such as stroke. Many biomarkers associated with various CNS disorders are known. For example, see Henley et al., Curr. Opin. Neurol., 18:698-705, 2005, incorporated herein by reference in its entirety. The diagnostic determination done preferably includes neuroimaging. For example, see Mathis et al., Arch. Neurol., 62: 196-200, 2005, incorporated herein by reference in its entirety. In a preferred embodiment, the diagnostic determination involves a genetic test.

The methods also preferably involve pre-operative imaging to stereotactically define the location of the targeted neuronal population.

In a highly preferred embodiment, the methods additionally comprise imaging during administration in order to monitor cannula positioning. In one embodiment, the method comprises use of a neuronavigation system, for example, see U.S. Patent Application Publication No. 2002/0095081, incorporated herein by reference in its entirety. In a preferred embodiment, the methods additionally comprise neuroimaging to monitor infusate distribution.

In one aspect, the invention provides methods for the treatment of a CNS disorder.

In a preferred embodiment, the invention provides methods for the treatment of Alzheimer's disease. The methods comprise administering NGF, or an active fragment or variant thereof, locally, and preferably intermittently, to cholinergic neurons of the basal forebrain.

In a preferred embodiment, the invention provides methods for the treatment of Alzheimer's disease. The methods comprise administering GDNF, or an active fragment or variant thereof, locally, and preferably intermittently, to cholinergic neurons of the basal forebrain.

In a preferred embodiment, the invention provides methods for the treatment of Parkinson's disease. The methods comprise administering GDNF, or an active fragment or variant thereof, locally, and preferably intermittently, to the striatum and/or midbrain.

In a preferred embodiment, the invention provides methods for the treatment of Parkinson's disease. The methods comprise administering VIP, or an active fragment or variant thereof, locally, and preferably intermittently, to the striatum and/or midbrain.

In a preferred embodiment, the invention provides methods for the treatment of Parkinson's disease. The methods comprise administering PTN, or an active fragment or variant thereof, locally, and preferably intermittently, to the striatum and/or midbrain.

In a preferred embodiment, the invention provides methods for the treatment of stroke. The methods comprise administering BMP, or an active fragment or variant thereof, locally, and preferably intermittently, to the CNS locus impacted by the stroke.

Table 1 provides a list of growth factors that can be used in the present invention to produce desired effects in a variety of target neuronal populations. This description is exemplary, and is not intended to be limiting.

More generally, Table 2 provides a list of growth factors that are generally able to produce beneficial effects, such as survival, neurite outgrowth and phenotypic maintenance, in the particular types of neurons listed. This description is exemplary, and not intended to be limiting.

The dose of growth factor delivered is determined by the particular growth factor, the target tissue density, the target tissue volume, and the tissue clearance rate. Typically, the amount of growth factor will be between about 1 µg and about 1000 µg, more preferably between about 1 µg and about 500 µg, more preferably between about 1 µg and about 250 µg, more preferably between about 1 µg and about 100 µg. In an especially preferred embodiment, the amount of growth factor is between about 10 µg and about 100 µg. In a preferred embodiment, following an intermission of from about 7 days to about 45 days, more preferably from about 14 days to about 45 days, more preferably from about 17 days to about 35 days, more preferably from about 20 days to about 35 days, delivery, if required, is repeated at a dose again designed to maintain a therapeutically effective amount of growth factor in tissue without producing harmful accumulation.

In a preferred embodiment, administration of the growth factor comprises two or more such intermissions.

In a preferred embodiment, the duration of a later occurring intermission is longer than the duration of an earlier occurring intermission in an administration regiment comprising three or more delivery steps.

In a preferred embodiment, the dose of growth factor given in an earlier delivery is greater than the dose of growth factor given in a later delivery in an administration regimen comprising two or more delivery steps.

It is further contemplated that the growth factor be administered with an effective amount of a second therapeutic agent. For example, in the treatment of Alzheimer's disease, such second therapeutic agents may include: cholinergic agonists, particularly those specific to the CNS and not to peripheral muscles, cholinesterase inhibitors such as tacrine hydrochloride, neurotrophins such as NGF, BDNF, NT-3, NT-4/5, basic fibroblast growth factor (bFGF), ciliary neurotrophic factor (CNTF), inhibitors of senile amyloid plaque formation, inhibitors of PHF formation, and inducers of endogenous neurotrophic factor synthesis or production.

The growth factor protein products according to this invention may be isolated or generated by any means known to those skilled in the art.

Naturally-occurring growth factor protein products may be isolated from mammalian neuronal cell preparations, or from a mammalian cell line secreting or expressing growth factor. For example, PCT International Publication No. WO93/06116, incorporated herein by reference in its entirety, describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding growth factor, cloning the gene in suitable vectors and cell types, modifying the gene if necessary to encode a desired variant, and expressing the gene in order to produce the growth factor protein product. Alternatively, a nucleotide sequence encoding the desired growth factor protein product may be chemically synthesized. It is contemplated that growth factor protein product may be expressed using nucleotide sequences which differ in codon usage due to the degeneracies of the genetic code or allelic variations.

In some embodiments herein, growth factor is administered in the form of an encoding nucleic acid that may be expressed in a transduced cell. In one embodiment, a high molecular weight neurotherapeutic is administered to a patient, wherein the high molecular weight neurotherapeutic comprises a nucleic acid encoding a growth factor, wherein the nucleic acid is expressed in a transduced CNS cell of the patient and the encoded growth factor is produced. Thus, the growth factor is produced in situ. Nucleic acids encoding growth factor proteins of the invention are well known in the art.

In a preferred embodiment, the nucleic acid encoding a growth factor is regulatable in situ. In one embodiment, a pharmaceutical composition comprising a vector comprising a nucleic acid encoding a growth factor under the control of a regulatable promoter is administered. It will be appreciated that regulatable expression of a nucleic acid encoding a growth factor provides for intermittent delivery of growth factor.

A therapeutic infusate composition is a volume of pharmaceutical composition to be delivered by CED in a single administration. The volume of infusate will be largely determined by the target tissue and its volume. Typical volumes will be between about 10 µl and about 10 cc, though larger and smaller volumes may be used.

The term "target tissue" refers to a physical (usually anatomical) target in the CNS comprising a neuronal population of interest.

A tracing agent is preferably detectable by magnetic resonance imaging (MRI) or X-ray computed tomography. The distribution of tracing agent is monitored and used as an indirect measure of the distribution of growth factor or high molecular weight neurotherapeutic. This monitoring is done to verify that the growth factor is reaching target tissue and achieving an effective concentration therein and to detect unwanted delivery of infusate to non-target tissue.

In a preferred embodiment, a tracing agent is separate from the growth factor. The tracing agent is distributed in a manner that correlates with that of the growth factor and thus is an indirect indicator of growth factor distribution.

In a preferred embodiment, the tracing agent and the growth factor are each in the form of carrier compositions, which confers highly similar distribution characteristics thereto.

In a highly preferred embodiment, the tracing agent and the growth factor are in the form of liposomal compositions. Liposome-based tracing agents are very highly accurate indirect indicators of the distribution of liposome-based high molecular weight neurotherapeutics.

The act of "monitoring" refers to obtaining serial images of the tracing agent over time. By monitoring the distribution of the tracing agent, the location and volume of distribution of the high molecular weight neurotherapeutic within the tissue may be determined at any time during the infusion process. Serial images may be obtained at any rate up to the maximum rate that the imaging instrument can obtain images. For example, serial images may be obtained at intervals ranging from a few milliseconds to hours, but more typically at intervals of minutes, such as intervals of 1, 2, 5, 10, 15, 20 or 30 minutes. The interval between serial images may be varied during infusion. In some instances, it may be desirable to obtain images at short intervals (for example, every 5, 10, or 15 seconds) at the beginning of the infusion process to detect backflow along the cannula, or to verify that the infusate is entering the desired target tissue. Once delivery to the proper site is confirmed, the interval between images may be lengthened, and the images used to follow the progress of infusion.

In one aspect, the invention provides treatment methods that comprise delivering a pharmaceutical composition of the invention by CED, wherein the pharmaceutical composition comprises a tracing agent, monitoring the distribution of the tracing agent as it moves through the CNS, and ceasing delivery of the pharmaceutical composition when the high molecular weight neurotherapeutic is distributed in a predetermined volume within the CNS. The movement of the tracing agent through the solid tissue may be monitored by an imaging technique such as magnetic resonance imaging (MRI) or X-ray computed tomography (CT). The tracing agent has a mobility in CNS tissue that is substantially similar to the therapeutic agent, and delivery is ceased when the tracing agent is observed to reach a desired region or achieve a desired volume of distribution, or to reach or nearly reach or exceed the borders of the target tissue.

The predetermined volume may correspond to a particular region of the brain. The predetermined volume of distribution is "substantially similar" to the volume of distribution observed for a tracing agent that is being monitored to follow the infusion. "Substantially similar" refers to a difference in volume of less than 20%. More preferably, the difference in volume is less than 15%, more preferably less than 10%, more preferably less than 5%. By monitoring the distribution of the tracing agent, infusion may be ceased when the predetermined volume of distribution is reached.

Volume of distribution may be determined, for example, by using imaging software that is standard in the art, e.g., iFLOW™. See also, for example, Krautze et al., Brain Res. Protocols, 16:20-26, 2005; and Saito et al., Exp. Neurol., 196:3891-389, 2005, incorporated herein by reference in its entirety.

Growth Factor Variants

The term "growth factor variant" as used herein includes polypeptides in which amino acids have been deleted from ("deletion variants"), inserted into ("addition variants"), or substituted for ("substitution variants"), residues within the amino acid sequence of naturally-occurring growth factor. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule is biologically active.

The term "biologically active" as used herein means that the fragment of variant demonstrates similar properties, but not necessarily all of the same properties, and not necessarily to the same degree, as the growth factor on which it is based.

Mutagenesis techniques for the replacement, insertion or deletion of one or more selected amino acid residues are well known to one skilled in the art (e.g., U.S. Pat. No. 4,518,584, the disclosure of which is hereby incorporated herein by reference in its entirety.) There are two principal variables in the construction of variants: the location of the mutation site and the nature of the mutation. In designing growth factor variants, the selection of the mutation site and nature of the mutation will depend on the growth factor characteristic(s) to be modified. The sites for mutation can be modified individually or in series, e.g., by (1) substituting first with conservative amino acid choices and then with more radical selections depending upon the results achieved (2) deleting the target amino acid residue, or (3) inserting amino acid residues adjacent to the located site. Conservative changes in from 1 to 20 amino acids are preferred. Once the amino acid sequence of the desired growth factor protein product is determined, the nucleic acid sequence to be used in the expression of the protein is readily determined. N-terminal and C-terminal deletion variants may also be generated by proteolytic enzymes.

For growth factor deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other family members to modify the activity of a particular growth factor. Deletions in areas of substantial homology with other family sequences will be more likely to modify biological activity of the particular growth factor more significantly. The number of consecutive deletions will be selected so as to preserve the tertiary structure of the growth factor protein product in the affected domain.

Examples of variants include those disclosed in U.S. Pat. Nos. 6,723,701; 6,468,970; 6,440,702; 5,741,778; 5,731,284; 5,830,857; 5,733,875, each of which is incorporated herein by reference in its entirety.

For growth factor addition variants, amino acid sequence additions typically include N- and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include growth factor with an N-terminal methionyl residue (an artifact of the direct expression of GDNF in bacterial recombinant cell culture) and fusion of a heterologous N-terminal signal sequence to the N-terminus of growth factor to facilitate the secretion of mature growth factor from recombinant host cells. Such signal sequences generally will be obtained from, and thus be homologous to, the intended host cell species. Additions may also include amino acid sequences derived from the sequence of other growth factors.

Growth factor substitution variants have at least one amino acid residue of the growth factor amino acid sequence removed and a different residue inserted in its place. Such substitution variants include allelic variants, which are characterized by naturally-occurring nucleotide sequence changes in the species population that may or may not result in an amino acid change.

Specific mutations of the growth factor amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site.

Alternatively, the growth factor amino acid sequence may be modified to add glycosylation sites.

One method for identifying growth factor amino acid residues or regions for mutagenesis is called "alanine scanning mutagenesis" as described by Cunningham and Wells (Science, 244:1081-1085, 1989), incorporated herein by reference in its entirety. In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed growth factor variants are screened for the optimal combination of desired activity and degree of activity.

The sites of greatest interest for substitutional mutagenesis include sites where the amino acids found in a particular growth factor from various species are substantially different in terms of side-chain bulk, charge, and/or hydrophobicity. Other sites of interest are those in which particular residues of growth factor-related proteins, obtained from various species, are identical. Such positions are generally important for the biological activity of a protein. Initially, these sites are substituted in a relatively conservative manner. Such conservative substitutions are shown in Table 3 under the heading of exemplary substitutions. If such substitutions result in a change in biological activity, then more substantial changes (exemplary substitutions) are introduced, and/or other additions or deletions may be made, and the resulting products screened for activity.

Conservative modifications to the amino acid sequence (and the corresponding modifications to the encoding nucleic acid sequences) are expected to produce growth factor protein products having functional and chemical characteristics similar to those of natural growth factor correlate. In contrast, substantial modifications in the functional and/or chemical characteristics of growth factor protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Non-conservative substitutions may involve the exchange of a member of one of these classes for another. Such substituted residues may be introduced into regions of the growth factor protein that are homologous with other growth factor proteins, or into the non-homologous regions of the molecule.

Growth Factor Derivatives

Chemically modified derivatives of growth factor or growth factor variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed growth factor, or variants thereof, linked to at least one polyethylene glycol molecule, as well as use of growth factor, or variants thereof, attached to one or more polyethylene glycol molecules via an acyl or alkyl linkage.

Pegylation may be carried out by any of the pegylation reactions known in the art. See, for example: Focus on Growth Factors, 3 (2):4-10 (1992); EP 0 154 316, the disclosure of which is hereby incorporated by reference in its entirety; EP 0 401 384, the disclosure of which is hereby incorporated by reference in its entirety; and the other publications cited herein that relate to pegylation, the disclosures of which are incorporated herein by reference in their entirety. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with the growth factor or variant. Any known or subsequently discovered reactive PEG molecule may be used to carry out the pegylation of growth factor protein or variant. A preferred activated PEG ester is PEG esterified to N-hydroxysuccinimide ("NITS"). As used herein, "acylation" is contemplated to include without limitation the following types of linkages between the therapeutic protein and a water soluble polymer such as PEG: amide, carbamate, urethane, and the like. See Bioconjugate Chem., 5:133-140 (1994), incorporated herein by reference in its entirety. Reaction conditions may be selected from any of those known in the pegylation art or those subsequently developed, but should avoid conditions such as temperature, solvent, and pH that would inactivate the growth factor or variant to be modified.

Pegylation by acylation will generally result in a poly-pegylated growth factor protein or variant. Preferably, the connecting linkage will be an amide. Also preferably, the resulting product will be substantially only (e.g., >95%) mono, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the growth factor protein or variant in the presence of a reducing agent. Pegylation by alkylation can also result in poly-pegylated growth factor protein or variant. In addition, one can manipulate the reaction conditions to favor pegylation substantially only at the a-amino group of the N-terminus of the growth factor protein or variant (i.e., a mono-pegylated protein). In either case of monopegylation or polypegylation, the PEG groups are preferably attached to the protein via a—CH2-NH— group. With particular reference to the —CH2-group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/growth factor protein (or variant) conjugate molecules (meaning growth factor protein or variant to which a polymer molecule has been attached substantially only (i.e., >95%) in a single location). More specifically, if polyethylene glycol is used, the present invention also encompasses use of pegylated growth factor protein or variant lacking possibly antigenic linking groups, and having the polyethylene glycol molecule directly coupled to the growth factor protein or variant.

Thus, presently preferred growth factor protein products according to the present invention are pegylated growth factor protein or variants, wherein the PEG group(s) is (are) attached via acyl or alkyl groups. As discussed above, such products may be mono-pegylated or poly-pegylated (e.g., containing 2-6, and preferably 2-5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714, incorporated herein by reference in its entirety). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable condition used to react a biologically active substance with an activated polymer molecule. Methods for preparing pegylated growth factor protein or variant will generally comprise the steps of (a) reacting a growth factor protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/growth factor protein (or variant) conjugate molecule will generally comprise the steps of: (a) reacting a growth factor protein or variant with a reactive PEG molecule under reductive alkylation conditions, at a pH suitable to permit selective modification of the a-amino group at the amino terminus of said growth factor protein or variant; and (b) obtaining the reaction product(s).

For a substantially homogeneous population of mono-polymer/growth factor protein (or variant) conjugate molecules, the reductive alkylation reaction conditions are those which permit the selective attachment of the water soluble polymer moiety to the N-terminus of growth factor protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3-9, preferably 3-6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any growth factor protein or variant having an a-amino group at the amino terminus, and provide for a substantially homogenous preparation of monopolymer/growth factor protein (or variant) conjugate. The term "monopolymer/growth factor protein (or variant) conjugate" is used here to mean a composition comprised of a single polymer molecule attached to a molecule of growth factor protein or growth factor variant protein. The monopolymer/growth factor protein (or variant) conjugate preferably will have a polymer molecule located at the N-terminus, but not on lysine amino side groups. The preparation will preferably be greater than 90% monopolymer/growth factor protein (or variant) conjugate, and more preferably greater than 95% monopolymer/growth factor protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

Growth Factor Pharmaceutical Compositions

Growth factor pharmaceutical compositions typically include a therapeutically effective amount of a growth factor protein product in admixture with one or more pharmaceutically and physiologically acceptable formulation materials. Suitable formulation materials include, but are not limited to, antioxidants, preservatives, coloring, diluting agents, emulsifying agents, suspending agents, solvents, fillers, bulking agents, buffers, delivery vehicles, diluents, and excipients. For example, a suitable vehicle may include water, physiological saline solution, or artificial CSF, possibly supplemented with other materials. Neutral buffered saline or saline mixed with serum albumin are further exemplary vehicles.

Once the therapeutic composition has been formulated, it may be stored in sterile vials as a solution, suspension, gel, emulsion, solid, or dehydrated or lyophilized powder. Such formulations may be stored either in a ready to use form or in a form, e.g. lyophilized, requiring reconstitution prior to administration.

The optimal pharmaceutical formulation will be determined by one skilled in the art. See for example, Remington's Pharmaceutical Sciences, 18th Ed. (1990, Mack Publishing Co., Easton, Pa. 18042) pages 1435-1712, the disclosure of which is hereby incorporated by reference. The final dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. As studies are conducted, further information will emerge regarding the appropriate dosage levels for the treatment of various diseases and conditions.

The pharmaceutical composition can typically include an effective amount of the respective growth factor in combination with a pharmaceutically acceptable carrier and, in addition, may include other medicinal agents, pharmaceutical agents, carriers, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

In a preferred embodiment, growth factor is selected from the group consisting of NGF, BDNF, NT-3, NT-4/5, NT-6, GDNF, CNTF, LIF, IGF-1, b-FGF, neurturin, persephin, artemin, TGFa, TGFb, IGF-2, PDGF, EGF, cardiotropin, EGF, IGF, VEGF, Sonic hedgehog (SHH), BMPs, FGF20, VIP, PDGF, pleiotrophin (PTN), and HGF.

In a preferred embodiment, a pharmaceutical composition of the invention is locally deliverable into the mammalian CNS by CED.

In a preferred embodiment, the pharmaceutical composition comprises a tracing agent.

A tracing agent preferably comprises a paramagnetic ion for use with MRI. Suitable metal ions include those having atomic numbers of 22-29 (inclusive), 42, 44 and 58-70 (inclusive) and have oxidation states of +2 or +3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III).

In a preferred embodiment, the tracing agent comprises an MRI magnet that may be used in conjunction with MRI to monitor distribution of infused pharmaceutical composition.

In a preferred embodiment, the MRI magnet is gadolinium chelate.

In a preferred embodiment, the tracing agent comprises a liposome, which comprises an MRI magnet. In a preferred embodiment, the MRI magnet is gadolinium chelate.

In embodiments wherein X-ray imaging (such as CT) is used to monitor CED, the tracer may comprise a radiopaque material. Suitable radiopaque materials are well known and include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosumetic acid, iotasul, iotetric acid, iothalamic acid, iotroxic acid, ioxaglic acid, ioxotriroic acid, ipodate, meglumine, metrizamide, metrizoate, propyliodone, and thallous chloride.

In a preferred embodiment, the pharmaceutical composition comprises a facilitating agent. A facilitating agent is capable of facilitating the delivery of growth factor to target tissue, preferably when both facilitating agent and growth factor are delivered by CED. In a preferred embodiment, a facilitating agent is a biomolecule that is efficiently cleared from tissue. In a preferred embodiment, a facilitating agent has a short half life relative to growth factor. In a preferred embodiment, a facilitating agent is capable of competing with growth factor for binding to growth factor binding sites in brain parenchyma, which binding sites are other than cognate growth factor receptors. For additional description of facilitating agents, see U.S. 2002/0114780.

Figure 2:
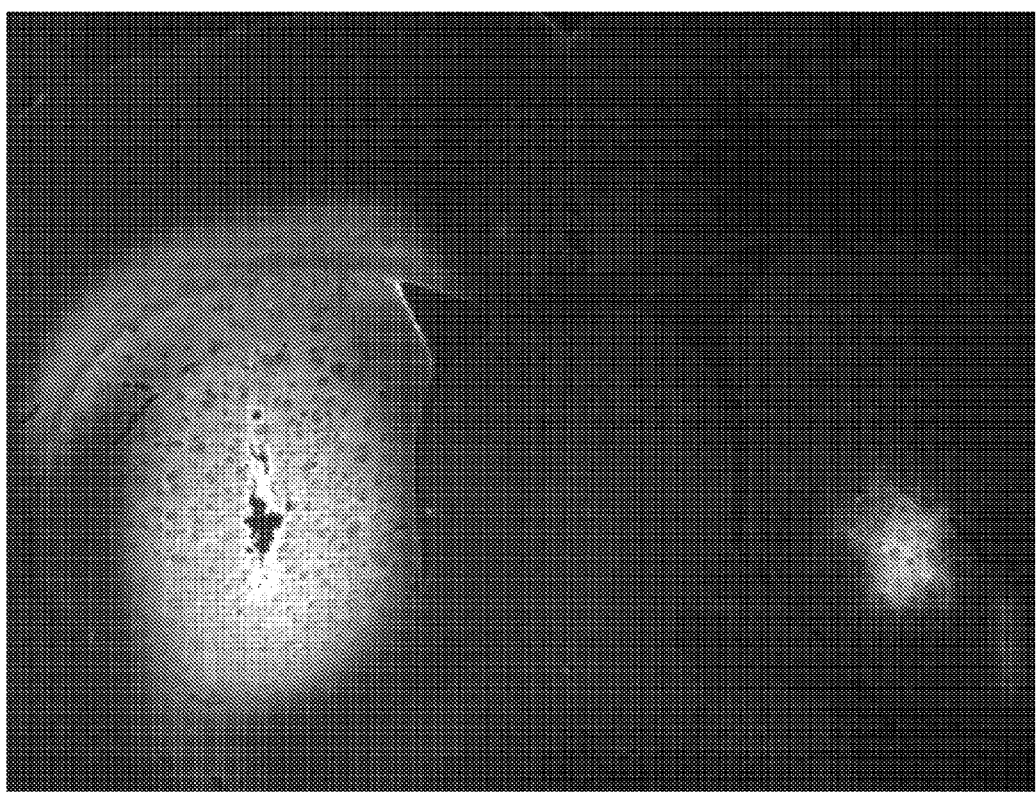

An especially preferred facilitating agent for use in the present invention is low molecular weight heparin. Low molecular weight heparin (LMW Hep) efficiently enhances the volume of distribution of infused GDNF, has a broad therapeutic window, and is safer than high molecular weight heparin (which may cause hemorrhage at same dose). When LMW Hep (1 microgram/microliter) with GDNF is infused a large improvement of the GDNF distribution is seen (FIGS. 1 and 2). High molecular weight heparin is an unfractionated form with a molecular weight range of 5,000-35,000 daltons High Molecular Weight Neurotherapeutics In one embodiment, growth factors are provided as high molecular weight neurotherapeutics. High molecular weight neurotherapeutic compositions of the invention comprise a growth factor and a carrier. In one aspect, the invention provides pharmaceutical compositions comprising high molecular weight neurotherapeutics. Further regarding high molecular weight neurotherapeutics, see U.S. provisional patent application Ser. No. 60/795,371 filed on Apr. 26, 2006, incorporated herein by reference in its entirety, and U.S. provisional patent application Ser. No. 60/900,492 filed on Feb. 9, 2007, incorporated herein by reference in its entirety.

High molecular weight neurotherapeutics of the invention have a molecular weight greater than about 200 kDa, more preferably greater than about 500 kDa, more preferably greater than about 1000 kDa, more preferably greater than about 1500 kDa, more preferably greater than about 2000 kDa, more preferably greater than about 2500 kDa, more preferably greater than about 3000 kDa, more preferably greater than about 3500 kDa, more preferably greater than about 4000 kDa, more preferably greater than about 4500 kDa, more preferably greater than about 5000 kDa, more preferably greater than about 5500 kDa, more preferably greater than about 6000 kDa, more preferably greater than about 6500 kDa, more preferably greater than about 7000 kDa, more preferably greater than about 7500 kDa, more preferably greater than about 8000 kDa, more preferably greater than about 8500 kDa, more preferably greater than about 9000 kDa, more preferably greater than about 9500 kDa, more preferably greater than about 10000 kDa.

In one embodiment, a high molecular weight neurotherapeutic of the invention has a diameter or length greater than about 10 nm, more preferably greater than about 20 nm, more preferably greater than about 30 nm, more preferably greater than about 40 nm, more preferably greater than about 50 nm, more preferably greater than about 60 nm, more preferably greater than about 70 nm, more preferably greater than about 80 nm, more preferably greater than about 90 nm, more preferably greater than about 100 nm, more preferably greater than about 110 nm, more preferably greater than about 120 nm. In some embodiments, a high molecular weight neurotherapeutic of the invention has a diameter or length greater than about 130 nm, or greater than about 140 nm, or greater than about 150 nm, or greater than about 160 nm, or greater than about 170 nm, or greater than about 180 nm, or greater than about 190 nm, or greater than about 200 nm.

In one embodiment, the carrier is a synthetic carrier.

A wide variety of synthetic carriers are available for use in the high molecular weight neurotherapeutics of the invention. In a preferred embodiment, the carrier is a liposome. In another preferred embodiment, the carrier is a metal particle, such as a gold particle, or a polymer. Regarding carriers, see, for example, Felgner et al., Ann NY Acad. Sci. 1995 Nov. 27; 772:126-39; Ramsay et al., Curr Drug Deliv. 2005 October; 2(4):341-51; Allen et al., Anticancer Agents Med. Chem. 2006 November; 6(6):513-23; Mitra et al., Curr Pharm Des. 2006; 12(36):4729-49, each of which is incorporated herein by reference in its entirety.

In one embodiment, the carrier is a naturally occurring composition or variant thereof. Examples of such carriers include virus particles, including modified virus particles (e.g., those having a modified surface protein profile). For example, see de Jonge, et al., Gene Therapy (2006) 13, 400-411, expressly incorporated herein in its entirety by reference.

In one embodiment, the high molecular weight neurotherapeutic is larger than an AAV virus.

In one embodiment, the high molecular weight neurotherapeutic has a higher molecular weight than an AAV virus.

In one embodiment, the high molecular weight neurotherapeutic comprises a carrier other than AAV.

Kits

In one aspect, the invention provides kits which comprise one or more pharmaceutical compositions of the invention. In one embodiment, a kit of the invention further comprises a delivery device useful for CED, preferably a cannula, and more preferably a step-design reflux-free cannula. In one embodiment, a kit of the invention further comprises a pump useful for CED. Kits may additionally comprise connecting parts, tubing, packaging material, instruction pamphlets, and other materials useful for practicing treatment of a CNS disorder.

Data Compilation

In one aspect, the invention provides methods of compiling data obtained from image-based monitoring of infusate distribution as delivered to patients having a CNS disorder. The data may include but is not limited to volume of infusate, volume of distribution, neuroanatomical distribution, neuroanatomical location of target population, genetic data, infusion parameters, cannula parameters, and cannula placement data. In one embodiment the invention provides a database comprising such data. In one embodiment, the database is useful for deriving algorithms describing the distribution of infusate in the CNS of a patient having a CNS disorder and may be used to model therapeutic delivery.

Delivery Devices

In one aspect, the invention provides a delivery device comprising a pump that is capable of delivering of a pharmaceutical composition of the invention, preferably by CED, preferably by intermittent CED. The device comprises, or is used in conjunction with a catheter or cannula that facilitates localized delivery to a CNS neuronal population. Preferably a CED-compatible, reflux-free step-design cannula which is compatible with chronic or acute administration is used. In a preferred embodiment, the device further comprises a pharmaceutical composition of the invention.

Any convection-enhanced delivery device may be appropriate for use. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.).

The catheter or cannula is inserted into CNS tissue in the chosen subject. One of skill in the art could readily determine which general area of the CNS is an appropriate target. For example, when treating Parkinson's disease, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target.

In a highly preferred embodiment, the method of CED is done with a CED-compatible reflux-free step design cannula. Such highly preferred cannulas are disclosed in Krauze et al., J. Neurosurg. 2005 November; 103(5):923-9. *Treatment of CNS Disorders*, incorporated herein by reference in its entirety.

Treatment generally results in reducing or preventing the severity or symptoms of the CNS disorder in the subject, i.e., an improvement in the subject's condition or a "therapeutic effect." Therefore, treatment can reduce the severity or prevent one or more symptoms of the CNS disorder, inhibit progression or worsening of the CNS disorder, and in some instances, reverse the CNS disorder.

As used herein, the term "ameliorate" means an improvement in the subject's condition, a reduction in the severity of the condition, or an inhibition of progression or worsening of the condition.

In the case of an acute CNS disorder, treatment will improve the subject's condition to a clinical endpoint, which may be amelioration of the disorder, complete or partial recovery from the disorder, at which point administration of growth factor is preferably discontinued.

An acute CNS disorder is one that may be effectively treated with administration of growth factor such that the subject's condition improves to a clinical point where administration may be discontinued. Examples of acute CNS disorders may include stroke and CNS trauma, though depending on severity, stroke and trauma may be considered chronic CNS disorders in need of chronic treatment (chronic growth factor administration).

The methods of the invention for treating a subject are applicable for prophylaxis to prevent a CNS disorder in a subject at risk for a CNS disorder, or to prevent clinical presentation in a subject diagnosed with a CNS disorder at an early stage.

The methods of the invention for treating a subject also can be supplemented with other forms of therapy. Supplementary therapies include drug treatment, a change in diet, etc. Supplementary therapies can be administered prior to, contemporaneously with or following the invention methods of treatment. The skilled artisan can readily ascertain therapies that may be used in a regimen in combination with the treatment methods of the invention.

It should be noted that the pharmaceutical compositions described herein may be used for veterinary as well as human applications and that the term "patient" should not be construed in a limiting manner.

All citations are expressly incorporated herein in their entirety by reference.

EXAMPLES

Example 1

GDNF Expression in the Rat Striatum after CED of AAV2-GDNF

AAV2-GDNF was infused into the striatum at different doses and rats were euthanized at different time points to analyze accumulation of GDNF expression. GDNF was measured by ELISA.

AAV2-GDNF(from Avigen)=1.1e13 vg/ml(PBS+ 0.001% pluronic F68)

Figure 3:
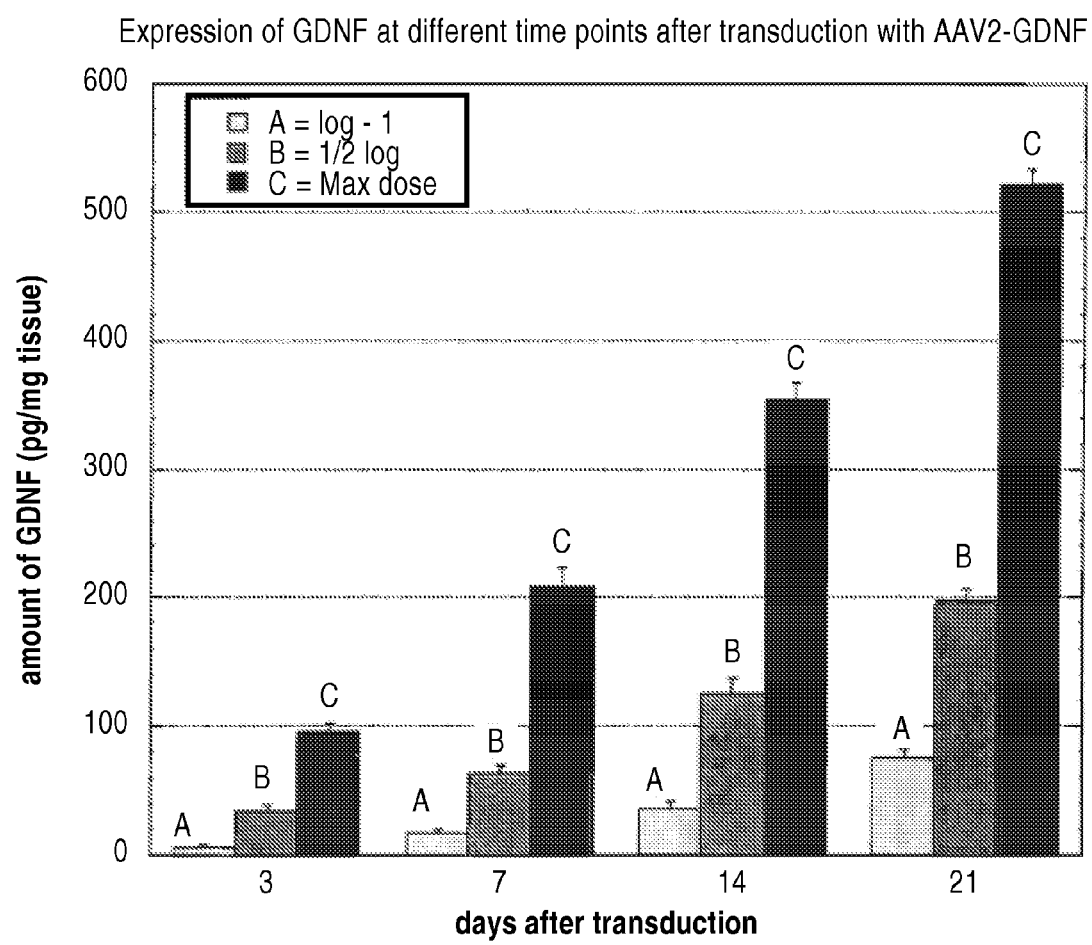
FIG. 3 is a graph illustrating expression of GDNF at different time points after transduction with AAV2-GDNF. AAV2-GDNF was infused into the striatum at different doses and rats were euthanized at different time points to analyze correlation with the level of GDNF expression. The results show gradual accumulation of GDNF over time.

3 different doses were chosen:
15 ml #max=1.65 e11vg [1.1e13 vg/ml]
15 ml #½ log=9.07e10vg [6.05e12 vg/ml]
15 ml #log−1=1.65e10 vg [1.1e12 vg/ml]
7 rats per time point:
group A: 4 rats $L_{hemisph}$: max/$R_{hemisph}$: ½ log [3 for ELISA, 1 for IHC]
group B: 3 rats $L_{hemisph}$: $log^{-1}$/$R_{hemisph}$: AAV2-LacZ (control) [3 for ELISA]
CED—infusion rate: 0.2 μl/min=11 min
0.5 μl/min=8 min
0.8 μl/min=11 min
15 μl 30 min
Results are provided in Table 4 and in FIG. 3, which demonstrate a gradual accumulation of GDNF over time.

Example 2

Evaluation of GDNF Protein Delivery in Treatment of Parkinson's Disease

Figure 4:
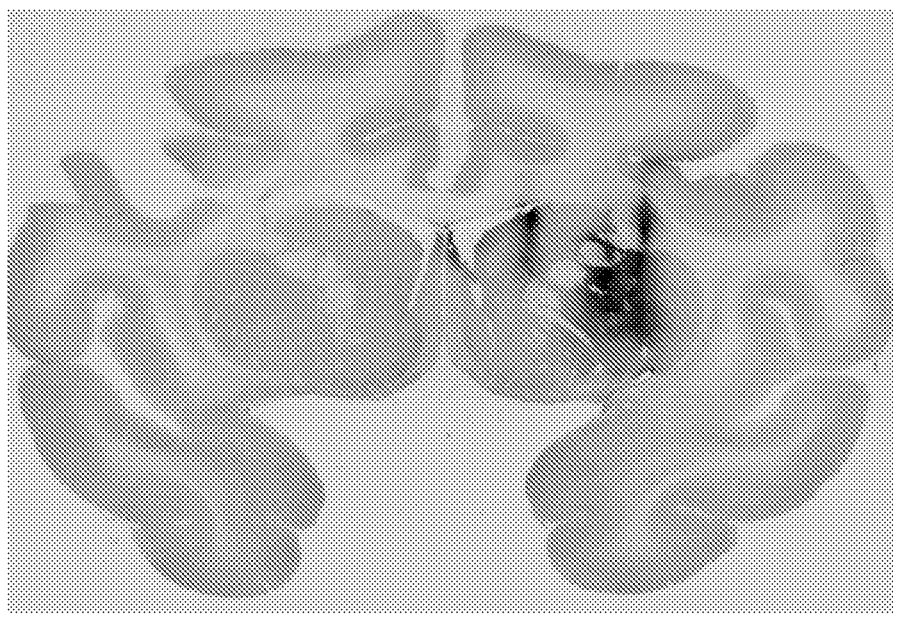
FIG. 4 is an image of a monkey brain treated according to a method of the invention. GDNF (30 µg/site) was administered by CED on one side of the normal monkey brain. One site was targeted in the caudate and 2 sites in the putamen. The monkey was euthanized 3 weeks later. Significant residual GDNF protein present. TH staining revealed strong upregulation of DA fibers on the GDNF-treated side only.

Single-dose administration of GDNF into monkey putamen results in prolonged tissue levels of GDNF that can last for longer than several weeks (FIG. 4).

In order to understand frequency and dose level of local administration of GDNF with convection-enhanced delivery (CED), the relationship between administration of a single dose and tissue half-life and biological effects (FIG. 4) is established. Further studies in MPTP monkeys with functional evaluation and PET imaging are optionally also done to further characterize the pharmacokinetics of locally administered GDNF in PD monkeys.

A dose-finding study in normal Rhesus monkeys to establish the magnitude and duration of response in dose-dependent fashion is done. Thirty-nine (39) animals are used and divided into cohorts of 3 animals. Each cohort receives unilaterally a dose of 10, 50 or 100 μg of GDNF into 2 sites in the putamen.

Figure 5:
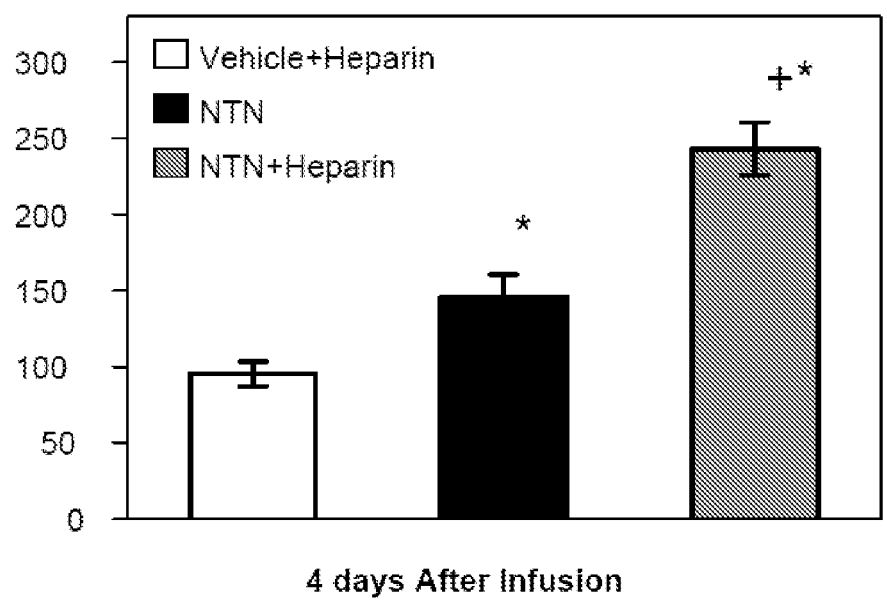
FIG. 5 is a graph illustrating effects of 5 µg of neuturin (NTN) administration into normal rats at 4 days. A significant increase in DA turnover was seen after single administration. An apparent synergy between NTN and heparin was observed as well.

The contralateral side is infused with PBS or excipient (see Table 5 and FIG. 5). Low molecular weight heparin is included in the formulation. Low molecular weight heparin significantly increases distribution of GDNF in the brain after CED, stabilizes GDNF protein in the solution, and increases effects of GDNF on DA turnover that may increase functional effects of GDNF. (Hamilton J. F., Morrison P. F., Chen M. Y., Harvey-White J, Pernaute R. S., Phillips H. S., Oldfield E. H., and Bankiewicz K. S. Heparin Co-infusion during Convection-Enhanced Delivery (CED) increases the distribution of the glial derived neurotrophic factor (GDNF) ligand family in rat striatum and enhances the pharmacological activity of neurturin. (2001) Experimental Neurology 168, 155-161), incorporated herein by reference in its entirety.

Each animal receives unilateral administration of GDNF into 2 sites in the putamen. PBS is delivered on the contralateral side. CED will be used for drug administration. Three normal monkeys are euthanized at 6 weeks to determine normal levels of GDNF and DOPAC/DA ratio since there may be contralatral effect of GDNF administration.

Abbreviated Methods:
Surgery

Each animal receives GDNF or PBS/excipient into 2 sites (50 μl per site) into the putamen with CED. Stereotactic coordinates are established based on MRI and reflux-resistant fused-silica cannulas are placed into the target sites. CED is controlled by external pump. After GDNF administration, CSF is collected via cisternal puncture, and animals are returned to their cages. CSF is collected at baseline and every 2 weeks from all of the monkeys (6-week animals CSF collected at baseline, and at 0, 2, 4, 6 weeks; 4-week animals at baseline, 0, 2 and 4 weeks; 2-week animals at baseline, 0, 2 weeks; 0-week and baseline and at 0 weeks. Blood samples are collected along with CSF samples. Immediately after GDNF administration (0 weeks) or at 2, 4 or 6 weeks later, animals are euthanized and their brains are removed (fresh). Brains are blocked into 3-mm slabs and immediately frozen. Vital organs are collected for future pathological evaluations.

Brain Processing:

Brains are processed for: 1—GDNF levels by Elisa; 2—DOPAC/DA levels by HPLC; 3—GDNF, TH. CD68, GFAP immunostaining; 4—H&E Frozen brain blocks are mounted into the cryostat and 6 coronal sections (20 μm) are collected from each block that contains putamen. Sections are post-fixed and stained for GDNF immunochemistry to determine extent of GDNF delivery. Putamen on both sides of the brain is dissected out and weighed to obtain wet weight. Tissue is homogenized, and processed for GDNF content by ELISA, and DA and metabolites by HPLC. Protein content of the samples is measured as well.

Results

GDNF immunostaining detects GDNF protein in the putamen at all time-points. Volume of distribution (Vd) of GDNF is reduced as a function of time. Confirmation of GDNF staining is used to cross-validate ELISA and HPLC data.

1. Tissue Clearance of GDNF after Single Administration

Figure 6:
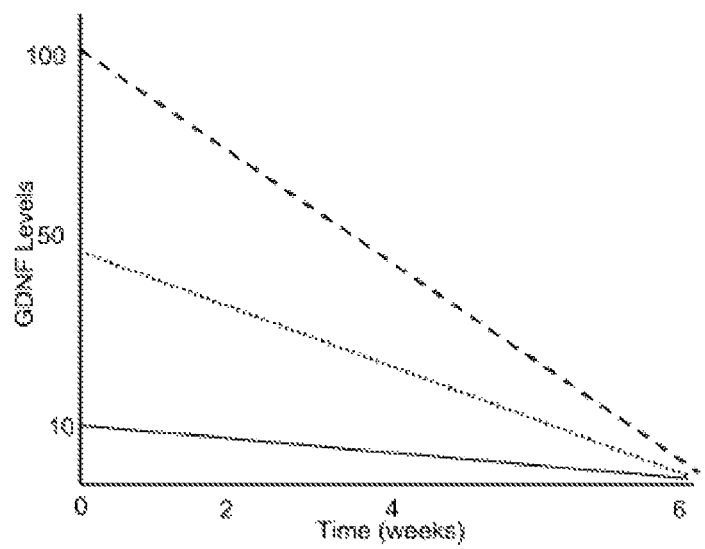
FIG. 6 is a graph illustrating tissue clearance of GDNF after single administration.
Figure 7:
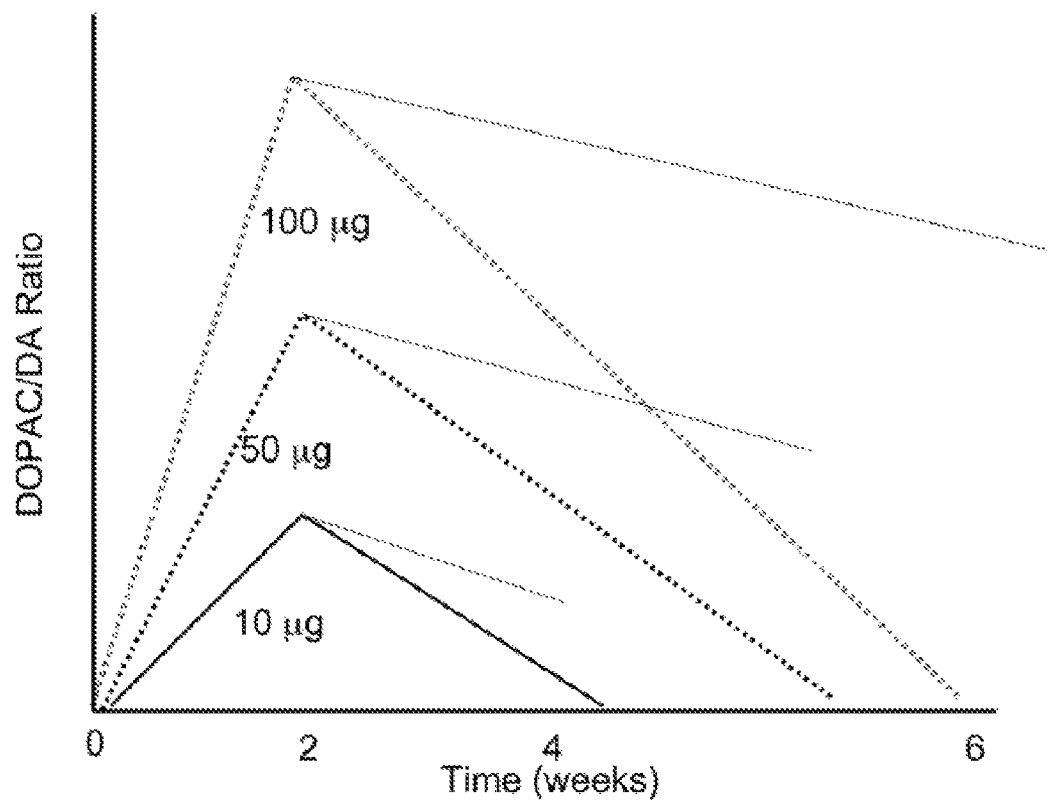
FIG. 7 is a graph illustrating regulation of DA levels after a single administration.

Referring to FIG. 6, following a single administration of 3 doses of GDNF into putamen, tissue levels of GDNF decline as a function of dose and time 2. Upregulation of DA Levels after Single Administration of GDNF FIG. 7 describes a possible outcome of a single-dose administration into putamen. Several scenarios are possible. (i) the pattern of DA upregulation will closely follow that of GDNF tissue levels, in which case the biological effect of GDNF is dependent on presence of GDNF protein. (ii) GDNF triggers biological effects, and they persist beyond detectable tissue levels of GDNF.

3. CSF Levels of GDNF

There may be a small increase in GDNF at 0 weeks with undetectable levels at all other times.

4. GDNF Antibodies

No GDNF Ab are detected at any time point in the CSF or serum5.

Neuropathological Findings

Although animals will not be perfused with formalin, cerebellum could be examined for any pathology. No pathology is observed.

Using the methods above, the relationship between a single dose of GDNF, its tissue half-life, and its biological effects on the DA system in monkeys are determined.

Subjects:
Species: Macaques (cynomolgus or rhesus)
Gender: Male or female
Age: young adult to adult
Number: 39
Wt.: 3-8 kg
Experimental Agent:
Glial derived neurotrophic factor (GDNF)
Treatment groups are shown in Table 6 and infusion parameters are shown in Table 7.
Assessment Schedule:
Magnetic resonance imaging (MRI)

Intracranial PBS/GDNF administration (via CED)

CSF and Blood Collection:

0-week survival: baseline and post-CED 2-week survival: baseline, post-CED and at 2 weeks post-surgery 4-week survival: baseline, post-CED and at 2 and 4 weeks post-surgery 6-week survival: baseline, post-CED and at 2, 4 and 6 weeks post-surgery Euthanasia:

Nine (9) animals euthanized after CED procedures

Nine (9) animals euthanized at 2-weeks post-surgery

Nine (9) animals euthanized at 4-weeks post-surgery

Nine (9) animals euthanized at 6-weeks post-surgery

Three (3) animals (PBS) euthanized at 6-weeks post-surgery

Necropsy and Tissue Processing:

After euthanasia, a cardiac perfusion is performed to systemically introduce 1 L of phosphate buffered saline. The brain is harvested, blocked into 3-mm slabs and freshly frozen in dry-ice cooled isopentane. Representative samples of the vital organs are harvested and processed for histological examination.

Brain Tissue Processing:

Frozen brain blocks are mounted into a cryostat and six (6) coronal sections (20 µm thickness) are collected from each blocks that contain the putamen. The sections are post-fixed and stained for GDNF immunohistochemistry to evaluate GDNF distribution.

Dissections are performed on the remaining frozen brain tissue to harvest the putamen nucleus from each block. The putamen tissue is weighed, homogenized, and processed for GDNF content by ELISA. DA and metabolite levels will be measured by HPLC.

Study Duration:

In-life duration: 0 to 6 weeks post CED infusion

In-Life Evaluation Parameters:

MRI

Intracranial PBS/GDNF administration

Post-surgery clinical observations

Weekly health observations

Blood collection (5 ml, serum): pre-surgery, post-CED and at 2, 4, and 6 weeks post-CED CSF collection (1 ml): pre-surgery, post-CED and at 2, 4, and 6 weeks post-CED Neuropathology And Biochemical Parameters:

GDNF antibody assay is performed on serum and CSF samples collected at pre-surgery, post CED, and at 2, 4, and 6 weeks post-CED GNDF assay is performed on CSF samples collected at pre-surgery, post CED, and at 2, 4, and 6 weeks post-CED Brain tissue analysis GDNF level determined by ELISA (primary endpoint)

DOPAC/DA ratio determined by HPLC (primary endpoint)

GDNF immunostaining (primary endpoint)

GFAP, TH, CD68 immunostaining (secondary endpoint)

H&E staining (primary endpoint)

See also Hadaczek et al., Human Gene Therapy, 17:1-12, 2006, incorporated herein by reference in its entirety.

Example 3

Evaluation of GDNF Expression in Rat Striatum

Figure 8:
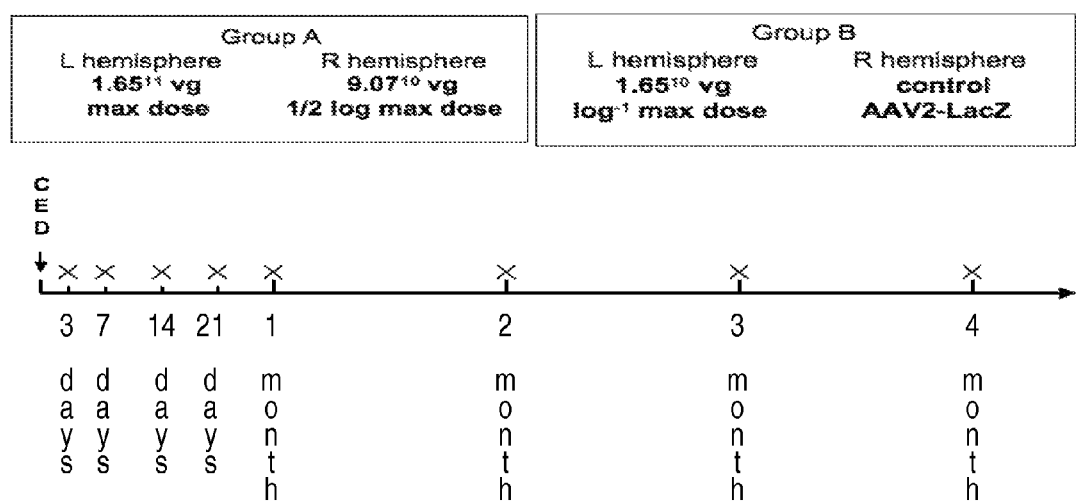
FIG. 8 illustrates AAV2-GDNF infused (CED) into the rat striatum at different doses.

AAV2-GDNF was infused (CED) into the rat striatum at different doses and rats were euthanized at different time points to analyze correlation with the level of GDNF expression overtime. Both hemispheres were infused with a proper amount of AAV2-GDNF in a total volume of 15 µl. The test groups are illustrated in FIG. 8.

Standard surgical procedures for intrastriatal CED were performed with the following infusion rates: 0.2 µl/min for 11 min, 0.5 µl/min for 8 min, and 0.8 µl/min for 11 min. Concentration of GDNF protein in striatal tissue was determined by ELISA. Following euthanasia, the brains were rapidly removed and the striatum was dissected bilaterally and immediately frozen. The samples were homogenized and exposed to acidification treatment. Tissue level of GDNF was determined in homogenates by GDNF $E_{max}$® ImmunoAssay System (Promega). To confirm GDNF expression, one rat from group A was used for immunohistochemical evaluation (standard DAB staining with anti human GDNF polyclonal antibody was used; R&D Systems, 1:50)

Figure 9:
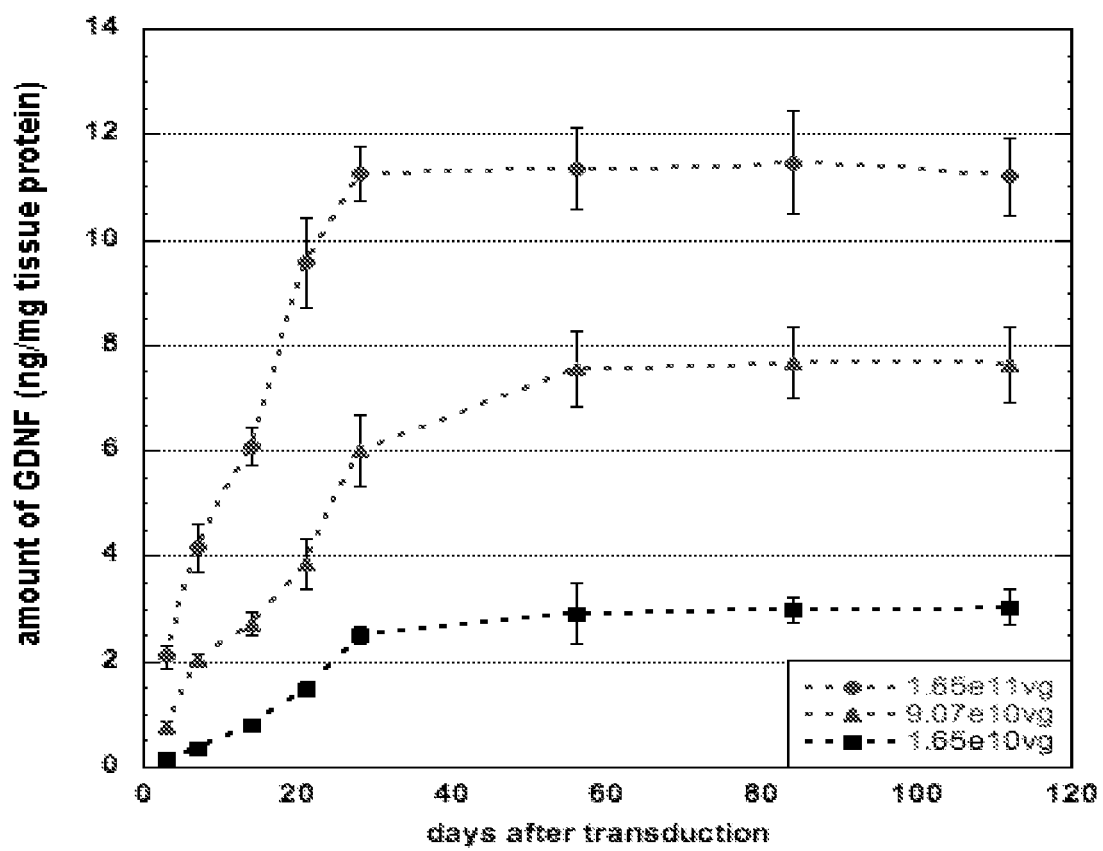
FIG. 9 is a graph illustrating expression of GDNF in the rat brain at different time points after transduction with AAV2-GDNF. The mean values in each time point were calculated from 3 hemispheres.

Results: Transduction of the rat striatum with AAV2-GDNF resulted in expression of GDNF protein in brain tissue in a dose dependant manner (FIG. 9). The level of GDNF expression was increasing up to 1 month when it reached its steady concentration within the striatal tissue. Since that time point, for the maximum dose of the virus infused ($1.65^{11}$ vg), the average amount of GDNF detected by ELISA was ~11 ng/mg tissue protein. Lower doses of the vector, $9.07^{10}$ vg and $1.65^{10}$ vg, resulted in lower GDNF tissue concentrations: ~6-7 ng/mg tissue protein and ~2-3 ng/mg tissue protein, respectively.

Example 4

Evaluation of GDNF Clearance from Rat Brain

Figure 10:
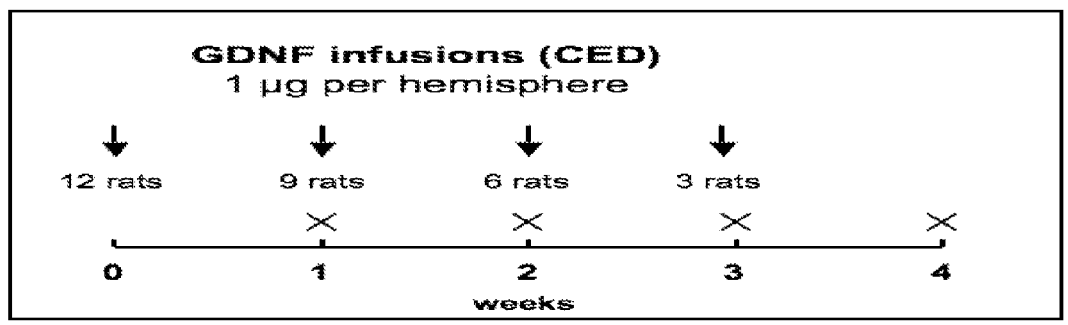
FIG. 10 illustrates experimental parameters for determining NF clearance from the rat brain.

Methods: To examine the GDNF clearance from the rat brain we designed the experiment in which we delivered GDNF protein into the striatum by means of CED. Both hemispheres were infused with 1 µg of GDNF in a total volume of 15 µl. We performed 4 weekly infusions to see if there is any accumulative effect. Every week 3 animals were euthanized for brain tissue collection. See FIG. 10.

Standard surgical procedures for intrastriatal CED were performed with the following infusion rates: 0.2 µl/min for 11 min, 0.5 µl/min for 8 min, and 0.8 µl/min for 11 min. Concentration of GDNF protein in striatal tissue was determined by ELISA. Following euthanasia, the brains were rapidly removed and the striatum was dissected bilaterally and immediately frozen. The samples were homogenized and exposed to acidification treatment. Tissue level of GDNF was determined in homogenates by GDNF $E_{max}$® ImmunoAssay System (Promega).

Figure 11:
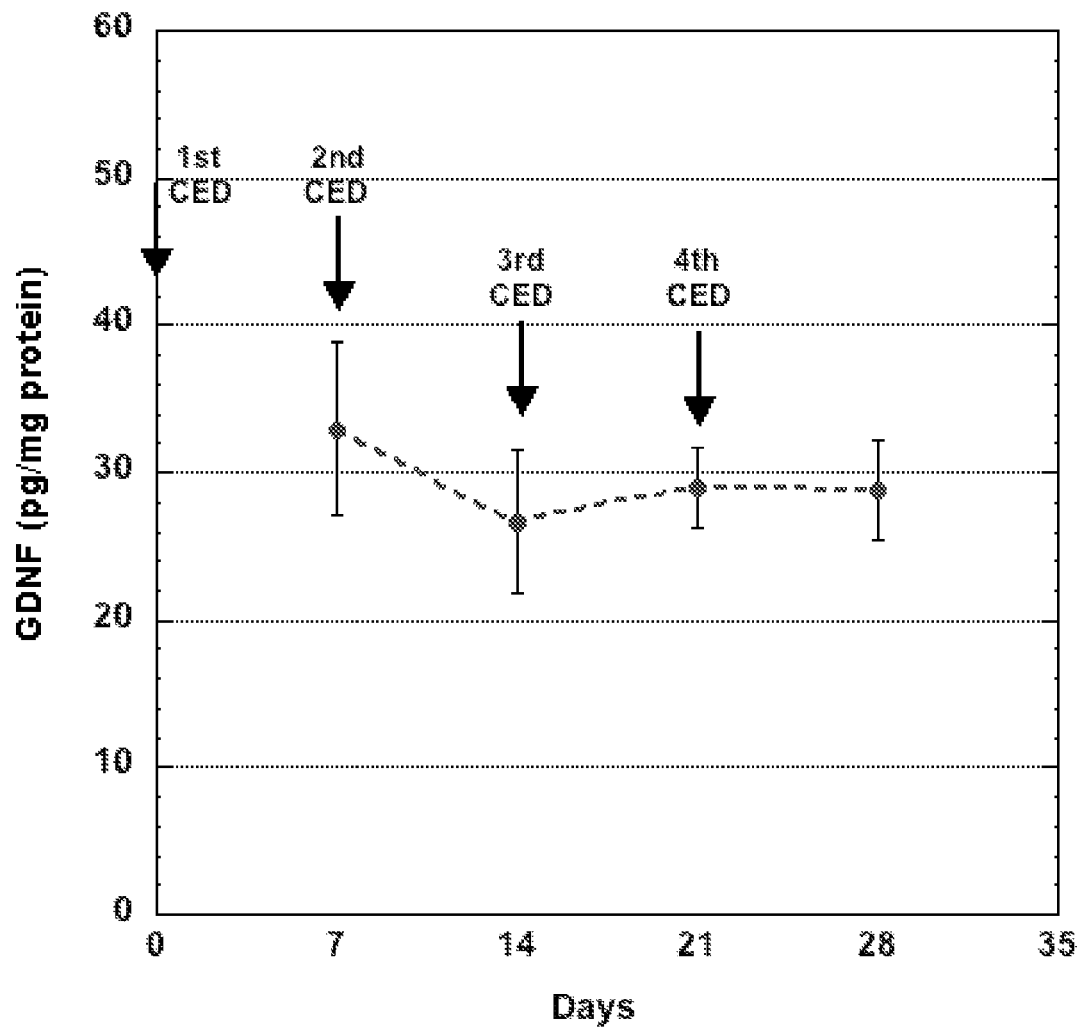
FIG. 11 is a graph illustrating clearance of GDNF protein in the rat brain after its weekly infusion by CED. The mean values in each week were calculated from 3 rats (6 hemispheres).

Results: Weekly delivery of GDNF protein into the rat striatum resulted in its steady level in the brain tissue. The average concentrations were 32.9; 26.6; 29.0; and 28.8 pg/mg protein in week 1, 2, 3, and 4 respectively. (FIG. 11)

Example 5

Time Course of GDNF Clearance from Rat Brain

GDNF protein was infused into the striatum and rats were euthanized at different time points to analyze the time course of GDNF clearance from the brain.

The amount of GDNF was measured by ELISA.

GDNF (from NIH; 10 µg/30 µl): 0.33 µg/µl

One dose was chosen:

The original stock was diluted 1:2 with PBS

40 µl+80 µl PBS=120 µl per line(0.11 µg/µl)

Figure 12:
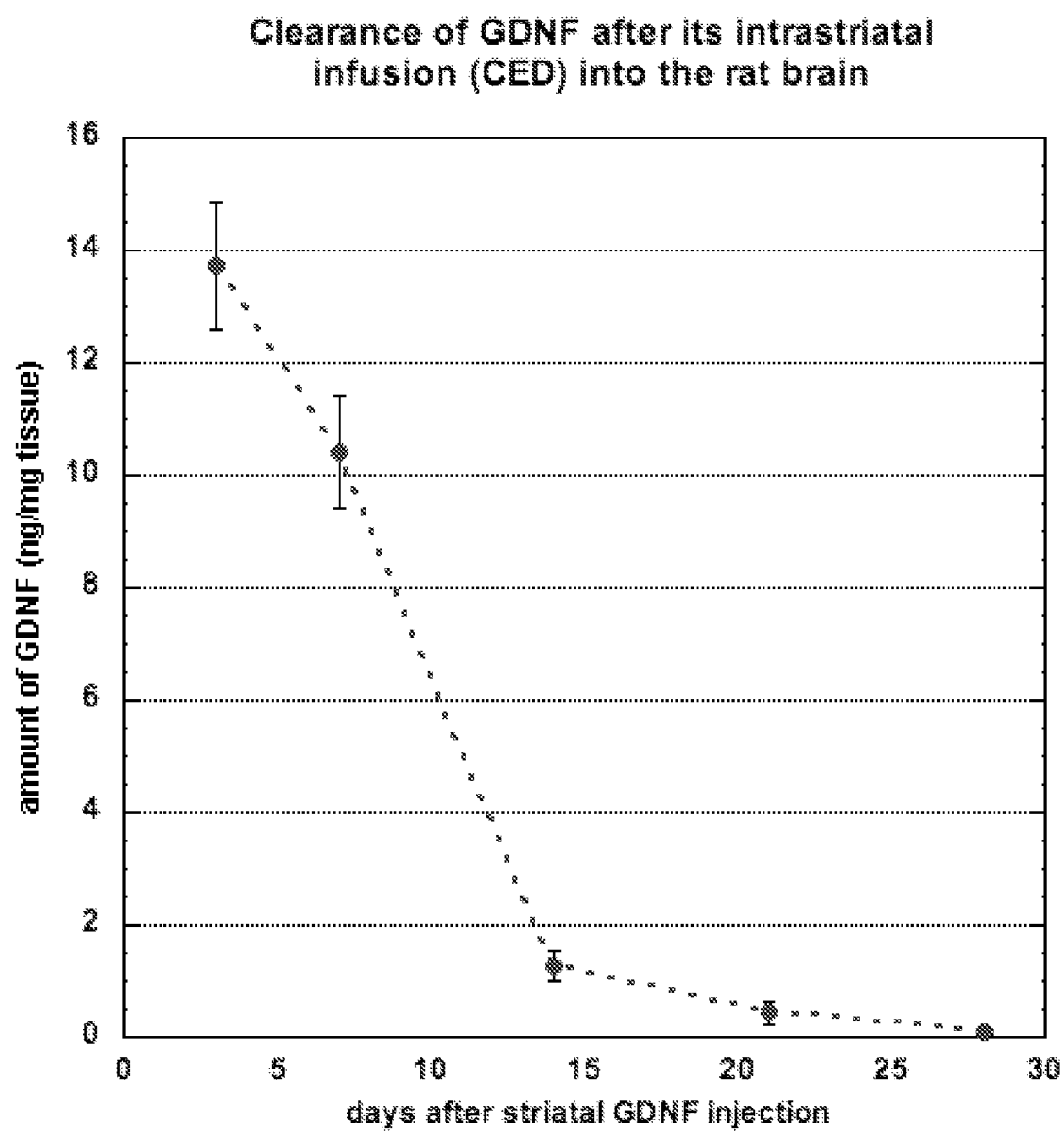
FIG. 12 is a graph illustrating clearance of GDNF after its intrastriatal infusion into the rat brain.

15 μl will be infused into each hemisphere
(total amount: 1.65 μg GDNF per hemisphere)
2 rats per time point (4 hemispheres)
CED infusion rate: 0.2 μl/min=11 min; 0.5 μl/min=8 min; 0.8 μl/min=11 min; 15 μl, 30 min total. (FIG. 12).

The following publications are incorporated herein by reference in their entirety: Varon et al., Ann. Rev. Neuroscience, 1:327, 1979; Thoenen et al., Science, 229:238, 1985); Thoenen, Trends. Neurosci. 14:165-170, 1991; Lapchak et at., Rev. Neurosci., 3:1-10, 1993; Bothwell, Ann. Rev. Neurosci., 18:223-253, 1995; Lapchak et al., Rev. Neurosci. 3:1-10, 1993; Bothwell, Ann. Rev. Neurosci., 18:223-253, 1995; Chao et al., TINS 18:321-326, 1995; Lin et al., Science 260:1130-1132, 1993; Krieglstein et al., EMBO J. 14:736-742, 1995; Poulsen et al., Neuron 13:1245-1252, 1994; Lin et al., Science 260:1130-1132, 1993; Hudson et al., Brain Res. Bull. 36:425-432; 1995; Beck et al., Nature 373:339-341, 1995; Tomac et al., Nature 373:335-339, 1995; Hoffer et al., Neurosci. Lett. 182:107-111, 1994; Oppenheim et al., Nature 373:344-346, 1995; Zurn et al., Neuroreport 6:113-118, 1994; Yan et al., Nature 373:341-344, 1995; Henderson et al., Science 266:1062-1064, 1994; Sariola et al., J. Cell Sci., 2003 Oct. 1; 116(Pt 19):3855-62; Venero et al., Neuroreport 4:959-962, 1993; Hefti, J. Neurobiol. 25:1418-1435, 1994; Olson, Neurochem. July 15:1-3, 1994; Batchelor et al., J. Comp. Neurol. 284:187-204, 1989; Kiss et al., Neurosci. 27:731-748, 1988; Woolf et al., Neurosci. 30:143-152, 1989; Selkoe, Neuron, 6:487-498, 1991; Hefti, J. Neurobiol. 25:1418-1435, 1994; Petty et al., Ann. August 36:244-246, 1994; Eslamboli, Rev. Neurosci., 2005; 16(4):303-10; Kordower et al., Ann. Neurol., 46:419-424, 1999; Gill et al., Nat. Med. 9:5899-595, 2003; Patel et al., Ann. Neurol., 57:298-302, 2005; Lang et al., Ann. Neurol., 59:459-466, 2006; Eslamboli, Rev. Neurosci., 2005; 16(4):303-10; Krauze et al., Exp Neurol. 2005 November; 196(1):104-11; Gill et al., Nat. Med. 9:5899-595, 2003.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiments that are known to those of ordinary skill in the art are expressly incorporated herein by reference and are intended to be encompassed by the present description and claims. Moreover, it is not necessary for a device or method to address each and every problem sought to be solved by the present invention, for it to be encompassed by the present description and claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

| Growth Factor | Target Population | Growth Factor Effect |
| --- | --- | --- |
| NGF | basal forebrain and hippocampus | survival of cholinergic neurons |
| NGF | nucleus basalis of Meynert | survival of cholinergic neurons |
| NGF | hippocampus | survival of cholinergic neurons |
| BDNF | hippocampus | survival of cholinergic neurons |
| NT-3 | hippocampus | survival of cholinergic neurons |
| CNTF | Striatum | survival of dopaminergic neurons |
| IGF-1 | hippocampus | protection against excitotoxic neuronal damage |
| GDNF | substantia nigra, striatum | neurite outgrowth and neuronal survival, dopaminergic neurons |
| VIP | substantia nigra, striatum | neurite outgrowth and neuronal survival, dopaminergic neurons |
| PTN | substantia nigra, striatum | neurite outgrowth and neuronal survival, dopaminergic neurons |
| bFGF20 | substantia nigra, striatum | neurite outgrowth and neuronal survival, dopaminergic neurons |

TABLE 2

| Neuronal Type | Growth Factor |
| --- | --- |
| Cholinergic | NGF |
| Cholinergic | BDNF |
| Cholinergic | NT-3 |
| Dopaminergic | CNTF |
| Dopaminergic | GDNF |
| Dopaminergic | VIP |
| Dopaminergic | bFGF |
| Dopaminergic | PTN |
| Glutaminergic | IGF-1 |

TABLE 3

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

TABLE 4

| Days after transduction | AAV2-LacZ control | AAV2-GDNF 1.65e10 vg $\log^{-1}$ | AAV2-GDNF 9.07e10 vg ½ log | AAV2-GDNF 1.65e11 vg max dose |
|---|---|---|---|---|
| 3 days | 2.2 ± 0.28 pg/mg | 7.0 ± 1 pg/mg | 34.4 ± 5 pg/mg | 96.4 ± 6 pg/mg |
| 7 days | 1.73 ± 0.13 pg/mg | 16.7 ± 3 pg/mg | 63.0 ± 7 pg/mg | 208.4 ± 15 pg/mg |
| 14 days | 2.37 ± 0.38 pg/mg | 36.1 ± 5 pg/mg | 127.0 ± 10 pg/mg | 354.0 ± 14 pg/mg |
| 21 days | 1.6 ± 0.12 pg/mg | 75.0 ± 7 pg/mg | 197.0 ± 10 pg/mg | 521.3 ± 12 pg/mg |

TABLE 5

Dose-Ranging Study In Normal Monkeys

| Time (weeks) | 10 µg | 50 µg | 100 µg | 0 µg |
|---|---|---|---|---|
| 0 | N = 3 | N = 3 | N = 3 | x |
| 2 | N = 3 | N = 3 | N = 3 | x |
| 4 | N = 3 | N = 3 | N = 3 | x |
| 6 | N = 3 | N = 3 | N = 3 | x |
| 6 | X | X | X | N = 3 |

TABLE 6

Treatment Groups

| Group | Left Hemisphere | Right Hemisphere dose/site (µg) | No. of animals | Survival Time (weeks) |
|---|---|---|---|---|
| 1 | PBS/excipient | 10 | 3 | 0 |
|   |   |   | 3 | 2 |
|   |   |   | 3 | 4 |
|   |   |   | 3 | 6 |
| 2 | PBS/excipient | 50 | 3 | 0 |
|   |   |   | 3 | 2 |
|   |   |   | 3 | 4 |
|   |   |   | 3 | 6 |
| 3 | PBS/excipient | 100 | 3 | 0 |
|   |   |   | 3 | 2 |
|   |   |   | 3 | 4 |
|   |   |   | 3 | 6 |
| 4 | PBS/PBS | 0 | 3 | 6 |

TABLE 7

Infusion Parameters

| Target Site | Infusion Rate (time) | Total Vol. per site | Total infusion time per site |
|---|---|---|---|
| Putamen (2 sites) | 0.2 µl/min (10 min.) 0.5 µl/min (10 min.) 0.8 µl/min (10 min.) 1.0 µl/min (10 min.) 1.5 µl/min (10 min.) 2.0 µl/min (5 min.) | 50 µl | 55 minutes |

What is claimed is:

1. A method of treating a human patient for Alzheimer's disease, comprising: administering to a target brain tissue of said patient a therapeutically effective amount of a pharmaceutical composition comprising a growth factor selected from: NGF, BDNF, NT-3, NT-4/5, NT-6, GDNF, CNTF, LIF, IGF-1, b-FGF, neurturin, persephin, artemin, TGFα, TGFβ, IGF-2, PDGF, EGF, cardiotropin, IGF, VEGF, Sonic hedgehog (SHH), BMP, FGF20, VIP, pleiotrophin (PTN), and HGF; wherein said growth factor is administered by intermittent convection enhanced delivery (CED) at a rate that counters the tissue clearance rate of said growth factor, wherein there is cessation of growth factor delivery during the intermissions between administrations, wherein the intermissions between administration of said growth factor are at least about one week, wherein said Alzheimer's disease is treated.

2. The method according to claim 1, wherein said pharmaceutical composition further comprises a tracing agent.

3. The method according to claim 2, wherein the tracing agent comprises an MRI magnet or a CT-detectable agent.

4. The method according to claim 2, wherein said tracing agent comprises a liposome.

5. The method according to claim 2, wherein said tracing agent is a gadolinium chelate.

6. The method according to claim 1, wherein said CED comprises incremental increases in flow rate.

7. The method according to claim 1, wherein the pharmaceutical composition is delivered with the use of a CED-compatible reflux-free step-design cannula.

8. The method according to claim 1, wherein said pharmaceutical composition comprises a high molecular weight neurotherapeutic comprising said growth factor and a carrier selected from: a liposome, a metal particle, a gold particle, a polymer, a virus particle, and a modified virus particle.

9. The method according to claim 1, wherein said pharmaceutical composition further comprises low molecular weight heparin as a facilitating agent.

10. The method according to claim 1, wherein said growth factor is BDNF.

11. The method according to claim 10, wherein the target tissue is cholinergic neurons of the hippocampus.

12. The method according to claim 10, wherein the target tissue is entorhinal cortex.

13. The method according to claim 1, wherein the intermissions between administration of said growth factor are between about 7 and 45 days.

14. The method according to claim 1, wherein the intermissions between administrations of said growth factor are between about 14 and 45 days.

15. The method according to claim 1, wherein the intermissions between administrations of said growth factor are between about 17 and 35 days.

16. The method according to claim 1, wherein the intermissions between administrations of said growth factor are between about 20 and 35 days.

17. The method according to claim 1, wherein cessation of delivery occurs when infusate is distributed throughout the substantial whole of the target brain tissue.

18. The method according to claim 1, wherein cessation of delivery occurs while infusate remains substantially confined to the target brain tissue.

19. The method according to claim 1, comprising three or more administrations, wherein the durations of two or more intermissions are varied in length of time.

20. The method according to claim 1, wherein the duration of intermissions increases over time.

* * * * *